US012150984B2

(12) United States Patent
Puleo et al.

(10) Patent No.: US 12,150,984 B2
(45) Date of Patent: Nov. 26, 2024

(54) DYSREGULATION OF TRAUMA REGULATION PATHWAY TREATMENT AND MONITORING TECHNIQUES

(71) Applicant: General Electric Company, Schenectady, NY (US)

(72) Inventors: Christopher Michael Puleo, Niskayuna, NY (US); Victoria Eugenia Cotero, Troy, NY (US); John Richard Nelson, Clifton Park, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 202 days.

(21) Appl. No.: 17/244,642

(22) Filed: Apr. 29, 2021

(65) Prior Publication Data
US 2021/0338805 A1 Nov. 4, 2021

Related U.S. Application Data

(60) Provisional application No. 63/018,749, filed on May 1, 2020.

(51) Int. Cl.
*C12N 13/00* (2006.01)
*A61K 39/215* (2006.01)
*C07K 14/54* (2006.01)
*C12N 15/86* (2006.01)
*A61K 39/00* (2006.01)

(52) U.S. Cl.
CPC ........ *A61K 39/215* (2013.01); *C07K 14/5412* (2013.01); *C12N 13/00* (2013.01); *C12N 15/86* (2013.01); *A61K 2039/53* (2013.01)

(58) Field of Classification Search
None
See application file for complete search history.

(56) References Cited

U.S. PATENT DOCUMENTS

| 8,725,251 | B2 | 5/2014 | Della Rocca et al. | |
|---|---|---|---|---|
| 2013/0131435 | A1* | 5/2013 | Della Rocca | A61F 7/00 604/113 |
| 2020/0046992 | A1* | 2/2020 | Tracey | A61B 5/6823 |

OTHER PUBLICATIONS

Morishita K, Karasuno H, Yokoi Y, Morozumi K, Ogihara H, Ito T, Fujiwara T, Fujimoto T, Abe K. Effects of therapeutic ultrasound on intramuscular blood circulation and oxygen dynamics. J Jpn Phys Ther Assoc. 2014; 17(1):1-7. doi: 10.1298/jpta.Vol17_001. PMID: 25792902; PMCID: PMC4316550.*
COVID-19 Treatments and Medications, https://www.cdc.gov/coronavirus/2019-ncov/your-health/treatments-for-severe-illness.html; accessed Apr. 28, 2023.*
Overview of COVID-19 Vaccines, https://www.cdc.gov/coronavirus/2019-ncov/vaccines/different-vaccines/overview-COVID-19-vaccines.html; accessed Apr. 28, 2023.*
Stoecklein VM., Osuka A, Lederer JA. Trauma equals danger—damage control by the immune system. J Leukoc Biol. Sep. 2012;92(3):539-51. doi: 10.1189/jlb.0212072. Epub May 31, 2012. PMID: 22654121; PMCID: PMC3427603.*
How Wounds Heal, MedlinePlus.gov, National Library of Medicine <https://medlineplus_gov/ency/patientinstructions/000741_htm>; accessed May 3, 2023.*
Herold, et al. J Allergy Clin Immunol. Jul. 2020; 146(1):128-136.e4. doi: 10.1016/j.jaci.2020.05.008. Epub May 18, 2020. PMID: 32425269 . . . (Year: 2020).*
Nguyen-Them, et al. Eur J Cancer. Jul. 2016;61:69-76. doi: 10.1016/j.ejca.2016.03.080. Epub May 5, 2016. PMID: 27156226. (Year: 2016).*
McElvaney OJ, et al. A linear prognostic score based on the ratio of interleukin-6 to interleukin-10 predicts outcomes in COVID-19. EBioMedicine 61, Oct. 8, 2020. (Year: 2020).*
McElvaney, Oliver J., et al.; "A linear prognostic score based on the ratio of interleukin-6 to interleukin-10 outcomes in COVID-19," EBioMedicine 61, Oct. 8, 2020, 8 pgs.

* cited by examiner

*Primary Examiner* — Benjamin P Blumel
*Assistant Examiner* — Jeffrey Mark Sifford
(74) *Attorney, Agent, or Firm* — Fletcher Yoder P.C.

(57) ABSTRACT

The subject matter of the present disclosure generally relates to techniques for addressing or correcting dysregulation of the trauma regulation pathway. The dysregulation may be associated with a physiological condition, such as a SARS-CoV-2 viral infection. In an embodiment, the techniques include treating dysregulation based on a renin-angiotensin pathway molecule or cell and/or a splenic pathway molecule or cell using targeted neuromodulation. In an embodiment, neuromodulation is used to regulate the immune system, e.g., as an energy-based adjuvant for a vaccine.

5 Claims, 23 Drawing Sheets

| ACE Inhibitors | IL6 Knock down | Anti-virals (RNA polymerase) | Ang receptor antagonists (AT1) |
|---|---|---|---|
| May increase the number of cases where COVID is "stopped in the nose" | Could help later stage patients by "checking" TH17 phenotypes | Could stop systemic spread of virus | Could stop at-risk patients from "Tripping" splenic pathway (i.e. Enable R-A compensation) |
| If it "goes to lungs"; It will make more people trip the splenic pathway and inhibit immune function | Direct autocrine action of IL21 may make this meaningless; May Impede CCK mechanism | If not taken prophylactically renin-angiotensin effect may have already occurred | If given too early could inhibit local immune reaction<br>(If given too late could make effect of splenic pathway more severe) |
| Need monitoring to ensure proper use | Need different or co-intervention | Need co-intervention | Need monitoring and/or co-intervention |

DYSREGULATION OF TRAUMA REGULATION PATHWAY TREATMENT AND MONITORING TECHNIQUES

CROSS-REFERENCE TO RELATED APPLICATIONS

The present application claims priority to and the benefit of U.S. Provisional Application No. 63/018,749, filed on May 1, 2020, and entitled "DYSREGULATION OF TRAUMA REGULATION PATHWAY TREATMENT AND MONITORING TECHNIQUES," the disclosure of which is incorporated by reference in its entirety herein.

BACKGROUND

The subject matter disclosed herein relates to techniques to address physiological conditions associated with dysregulation of the trauma regulation pathway.

In response to a wound or traumatic injury, the body activates or modulates the tissue renin-angiotensin system and local sensory neurons as part of a local response to the wound. As part of the local regulation, renin and angiotensin converting enzyme (ACE) act to activate angiotensin II, which in turn results in vasoconstriction, activation of the sympathetic nervous system, and activation of certain local immune responses among other effects. While local activation of the trauma regulation pathway is desirable in the context of wound response, dysregulation of this pathway may lead to inappropriate activation of the pathway in the absence of a wound or lack of downregulation of the pathway after activation.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one embodiment, a method for treating a subject with SARS-CoV-2 infection is provided that includes identifying a status of a trauma regulation pathway based on a presence or concentration of one or more molecules or cells or nerve signal associated with the status of the trauma regulation pathway; and administering a pharmaceutical composition to treat SARS-CoV-2 infection based on the status.

In one embodiment, a method for treating a subject with dysregulation of a trauma regulation pathway includes identifying a status of a trauma regulation pathway based on a presence or concentration of one or more molecules or cells or nerve signals associated with the status of the trauma regulation pathway; and administering a pharmaceutical composition based on the status.

In one embodiment, a method for monitoring a subject with dysregulation of a trauma regulation pathway includes identifying a baseline status of a trauma regulation pathway based on a presence or concentration of one or more molecules or cells associated with the trauma regulation pathway; administering a pharmaceutical composition; and monitoring changes from the baseline status of the trauma regulation pathway by measuring the presence or the concentration of the one or more molecules or cells after the administering.

In one embodiment, a method for treating a subject includes applying ultrasound energy to an internal tissue of the subject having a viral or pathogen infection to cause a change to a molecular component of a trauma regulation pathway in the subject to treat the viral infection, measuring the change or an indication of the change in the subject; and determining, based on the measuring, that the ultrasound energy caused the change to the molecule of the trauma regulation pathway to treat the subject.

In one embodiment, a method for treating a subject with SARS-CoV-2 infection, includes identifying a status of a trauma regulation pathway based on a presence or concentration of one or more molecules or cells or nerve signal associated with the status of the trauma regulation pathway; and applying ultrasound energy to an internal tissue of the subject to treat SARS-CoV-2 infection based on the status.

In one embodiment, a method for inducing an immunological response in a subject, includes administering a vaccine to the subject; and applying ultrasound energy to an internal tissue of the subject.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein:

FIG. 16 shows SARS-CoV-2 treatments and associated timing factors in accordance with embodiments of the disclosure;

DETAILED DESCRIPTION

One or more specific embodiments are described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to, "for example", "for instance", "such as", "e.g.", "including", "in certain embodiments", "in some embodiments", and "in one (an) embodiment."

When introducing elements of various embodiments of the present disclosure, the articles "a", "an", "the", and "said" are intended to mean that there are one or more of the elements. The terms "comprising", "including", and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Figure 1:
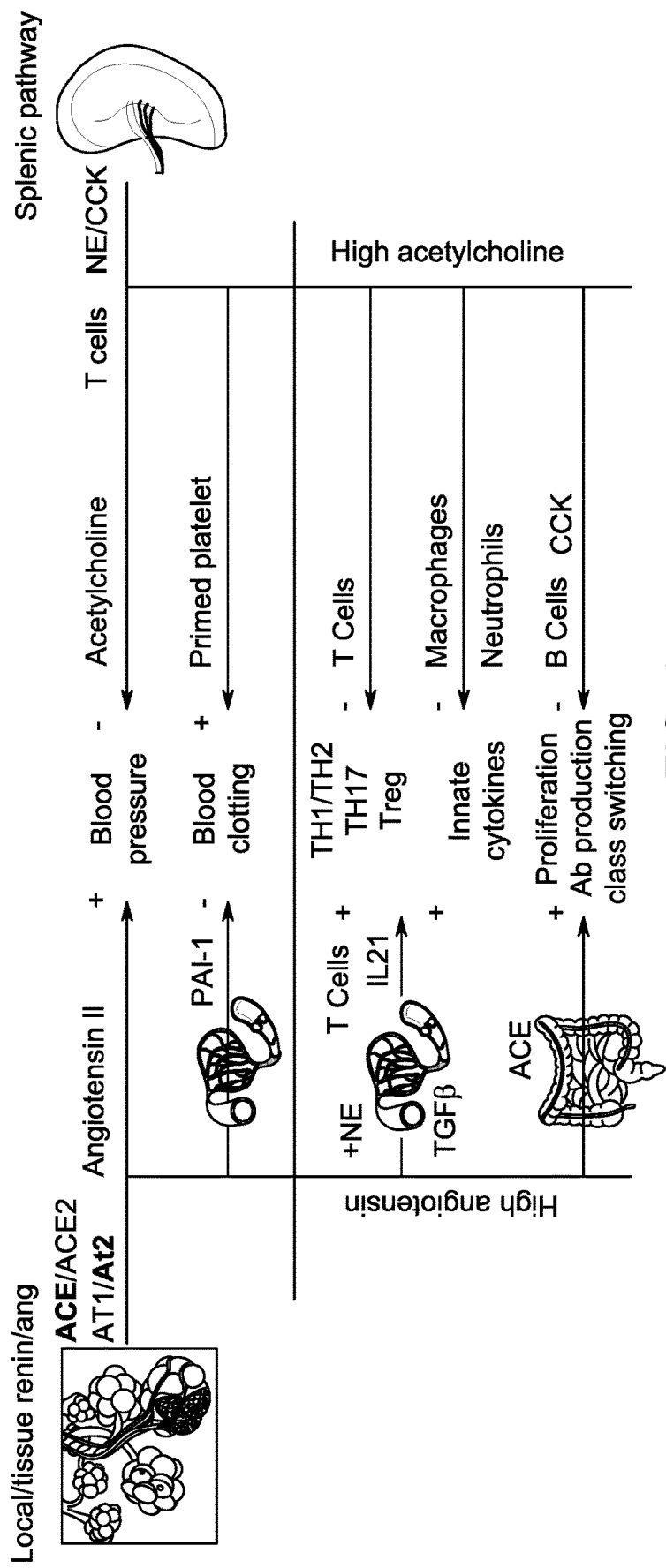
FIG. 1 is a schematic illustration of a trauma regulation pathway in accordance with embodiments of the disclosure.
Figure 2:
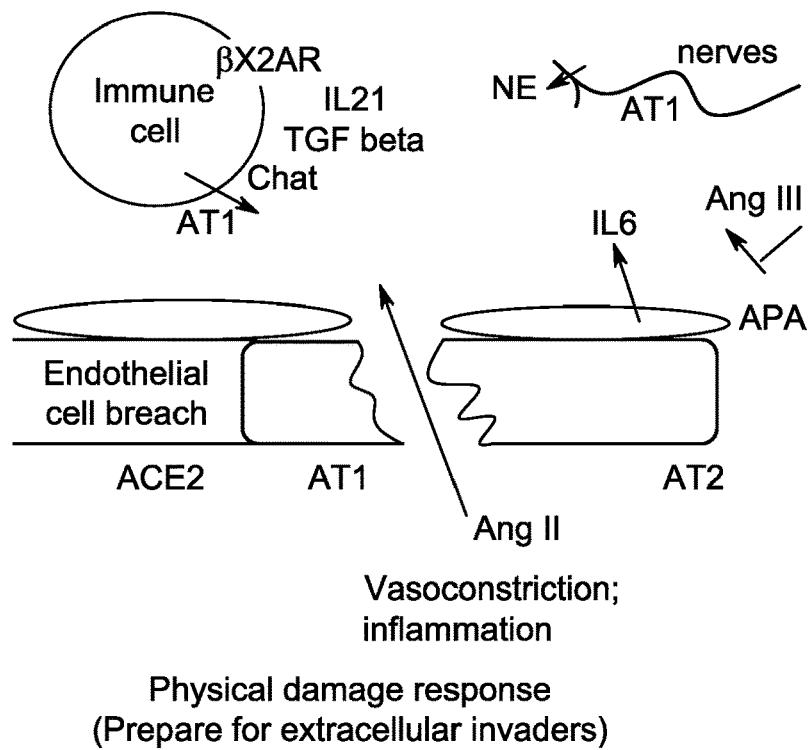
FIG. 2 is a schematic illustration of a physical damage response that activates a bacterial, fungal, or extracellular pathogen immune system response of the trauma regulation pathway (i.e. one that enables the body to defend physical damage to barrier tissue) in accordance with embodiments of the disclosure.
Figure 3:
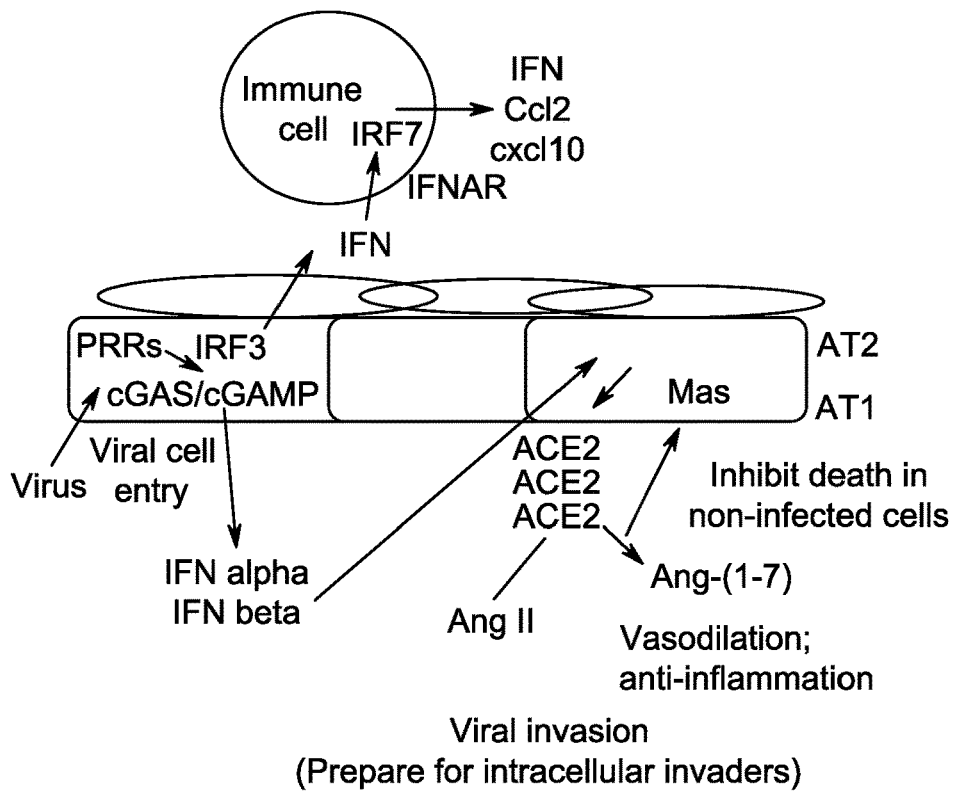
FIG. 3 is a schematic illustration of a response to viral infection of the trauma regulation pathway in accordance with embodiments of the disclosure.
Figure 4:
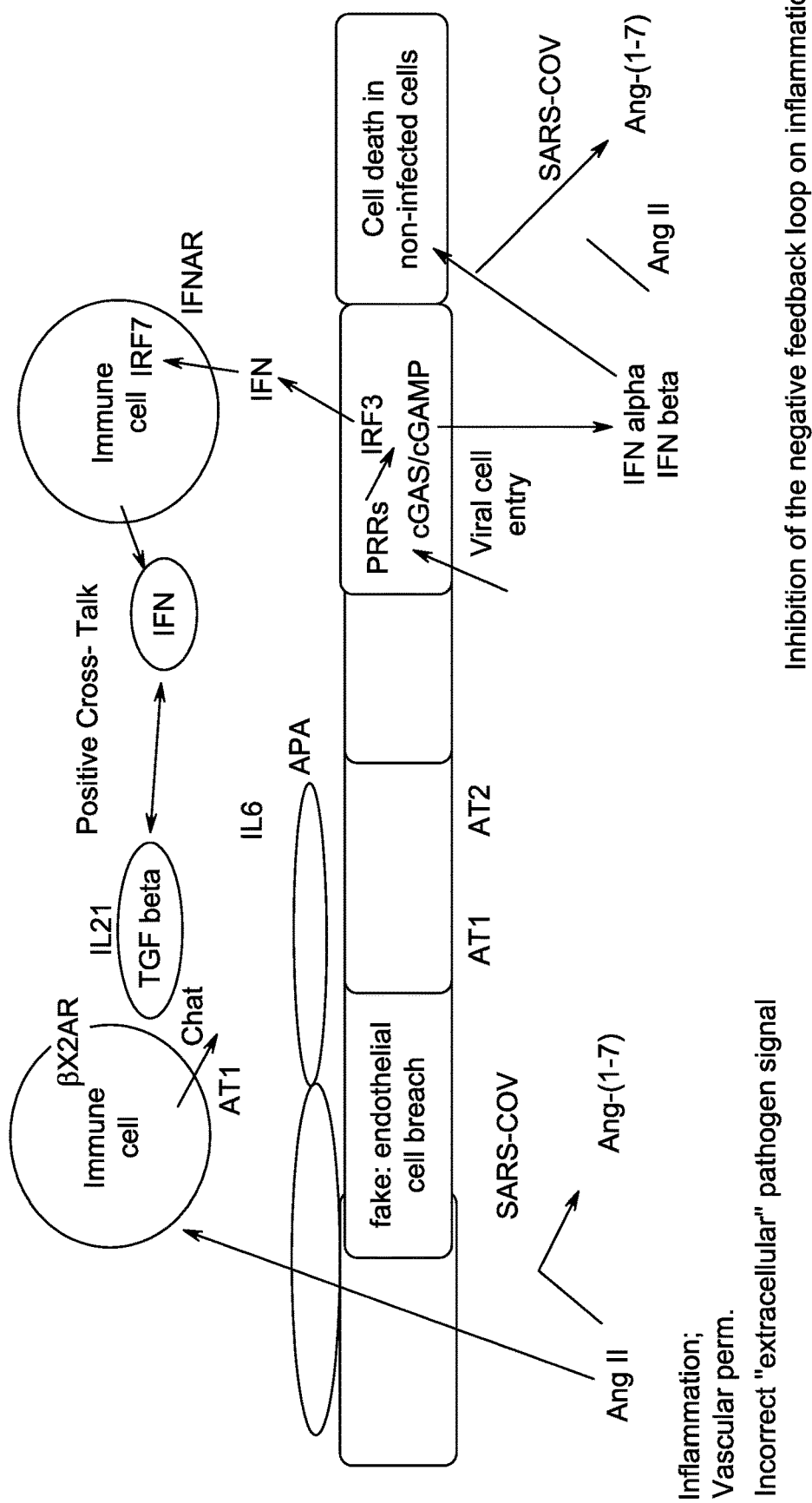
FIG. 4 is a schematic illustration of a dysregulated trauma regulation pathway in the context of SARS-CoV-2 infection in accordance with embodiments of the disclosure.

The disclosed embodiments relate to modulation of pathways involved in trauma regulation, e.g., local trauma response, as a technique for treating physiological conditions. The physiological conditions may include pathogen infections (e.g., bacterial, viral), sepsis, or inflammatory disorders. Certain features of this pathway are shown in FIG. 1. The activation of the trauma regulation pathway involves the renin-angiotensin system, which is involved in regulating blood pressure, and other sensory neurons within the peripheral nervous system, which sense both physical mechanical damage (via piezo receptors) and infection and inflammation (via TRPV family of ion channels). Renin is an enzyme produced and secreted by the kidneys in association with low blood pressure. Renin acts on angiotensinogen to form angiotensin I, which is converted to angiotensin II by angiotensin converting enzyme (ACE). Angiotensin II acts to raise blood pressure according to various mechanisms. Drugs to lower blood pressure target certain pathways in the renin-angiotensin system. ACE inhibitors inhibit the conversion of angiotensin I to angiotensin II. In addition, angiotensin II receptor antagonists and renin inhibitors have also been developed.

FIG. 1 shows an embodiment of local renin-angiotensin pathway activation in the lungs. It should be understood that the renin-angiotensin pathway activation as part of trauma regulation may be in additional or other locations in a patient. The disclosed embodiment is provided in the context of physiological conditions affecting the lungs, such as SARS-CoV-2 infection. Angiotensin-converting enzyme 2 (ACE2) is an enzyme attached to the outer surface (cell membranes) of cells in the oral and nasal mucosa, nasopharynx, lung, stomach, small intestine, colon, skin, lymph nodes, thymus, bone marrow, vascular wall, spleen, liver, kidney, and brain. ACE2 lowers blood pressure by catalyzing the hydrolysis of angiotensin II (a vasoconstrictor peptide) into angiotensin (1-7), a vasodilator. ACE2 also provides negative feedback to ANGII driven local tissue inflammation pathways, via the catalysis reaction described above. The ACE2 receptor is expressed on the alveolar type 2 (AT2) cells and in the vasculature wall of the alveoli in the highest concentration, permitting binding by SARS-CoV-2 virus on the receptor and resultant lung conditions. The renin-angiotensin response pathway affects both sides of the alveoli, the vascular components and also the air sacs. During infection, the vasculature may leak, allowing liquid into the air sac, which in turn may promote the lung deterioration exhibited by SARS-CoV-2 patients. Further, increased angiotensin 2 in this context affects blood pressure (constricts vessel wall) and reduces fluid clearance by the alveoli. Local sensory neurons are also responsive to the actions (i.e. blood pressure or inflammatory changes caused by angII and its derivatives) via mechanical/stretch and cytokine receptors.

As shown in FIG. 1, additional responses as part of the trauma regulation mediated by the renin-angiotensin system include regulation of plasminogen activator inhibitor-1 (PAI-1), which is a physiological inhibitor of fibrinolysis. Accordingly, increased PAI-1 expression promotes clotting by inhibiting breakdown of clots and clot removal while downregulation of PAI-1 has an anticoagulant effect. The renin-angiotensin system, when activated, also acts to regulate expression of certain local or circulating molecules, such as immune factors, neurotransmitters. In one example, altered expression of norepinephrine, TGF-beta, CCK, and/or cytokines (e.g., IL21) are observed as part of the renin-angiotensin response pathway. In another example, T cell expression is altered, and the presence or concentration of certain T cells locally or systemically is altered. The T cells may include TH1, TH2, TH17, and T regulatory cells. In another example, angiotensin-converting enzyme (ACE) in the intestines acts on cholecystokinin (CCK) to cleave c-terminal dipeptide, which may be associated with immune effects, such as proliferation of antibody production or class switching. The substrate CCK and angI compete for the active ACE site, and therefore CCK concentration within the intestines and circulation depends on the local renin-angiotensin system status. CCK and TGF-beta may also be involved in certain neurological pathways related to learning and memory. Accordingly, in an embodiment, dysregulation of the renin-angiotensin system may be associated with undesired neurological outcomes that may be treated by addressing the dysregulation. The presence of circulating cleaved dipeptide (Asp-Phe) may serve as a marker for ACE activity and, correspondingly, activity of the renin-angiotensin system as provided herein.

Provided herein are techniques that harness a splenic rapid response pathway that acts to counterbalance the activated renin-angiotensin system to provide signaling that reverses or counteracts or localizes the effects of the renin-angiotensin system. Treatments and/or monitoring techniques that target components of the splenic rapid response pathway may be beneficial in patients with a dysregulated trauma regulation pathway, such as inappropriate or hyper-activation of the renin-angiotensin system. As provided herein, treating or treatment refers to therapeutic treatment as well as prophylactic or preventative measures to cure or halt or at least retard disease progress. Those in need of treatment include those having a physiological condition associated with dysregulation of the trauma regulation pathway as well as those in need of prevention of such a condition. In an embodiment, the physiological condition may be a SARS-CoV-2 or SARS-CoV infection. In an embodiment, embodiments include prevention or reducing the spread of SARS-CoV-2 or inhibiting or reducing the onset, development or progression of one or more of the symptoms associated with infection with SARS-CoV-2. However, while certain embodiments of the disclosure are discussed in the context of SARS-CoV-2, it should be understood that other physiological conditions that feature dysregulation of the trauma regulation pathway may also be addressed via the disclosed techniques. Monitoring may be relative to a baseline status of one or more trauma regulation pathway molecules.

The splenic response of the trauma regulation pathway has various path functions that oppose the renin-angiotensin system and that may, alone or in combination, be used to mitigate or shut down undesired effects from dysregulation. Activation of the splenic pathway may include acetylcholine release (locally or systemically) that counteracts the vasoconstriction effect of angiotensin II to promote vasodilation. Additional effects may include regulation of primed platelets, macrophages, neutrophils, and B cells as well as production of CCK. The activated renin-angiotensin system may be generally associated with high angiotensin (local or systemic) while the activated splenic response pathway may be generally associated with high acetylcholine (local or systemic).

FIG. 2 shows an example of the renin-angiotensin system that is activated in response to physical damage to prepare for bacterial or fungal invaders that may take advantage of a breached tissue layer. The opening in the epithelial layer may be sensed via signaling receptors such as TRPv1 mediated stretch receptors that are sensitive to the stretching or physical damage in the epithelial tissue layer associated with a wound, and that act to promote vasoconstriction and inflammation response via release of certain molecules, such as IL-21, TGF-beta, IL-6, and norepinephrine. Accordingly, the schematic illustration of FIG. 2 may be a characteristic of a renin-angiotensin response to physical damage that acts to prevent bacterial or fungal infection.

In embodiments of the present disclosure, the response may be improperly activated in the absence of a wound or tissue breach. FIG. 3 is a schematic illustration of a virus response pathway in which no breach of the epithelial layer has occurred. The activated ACE2 and the immune response is different than the bacterial infection or physical damage response (FIG. 2), with molecules such as IRF7, IFN, Ccl2, cxcl10 involved. ACE2 causes vasodilation through hydrolysis of angiotensin II (a vasoconstrictor peptide) into angiotensin (1-7), a vasodilator. Accordingly, a vasodilation effect is seen in virus response rather than vasoconstriction, as in the wound response in FIG. 2. Viral entry into a particular cell also causes cell-specific responses that lead to cell death for infected cells as part of the viral response and inhibition of death in non-infected cells. In an embodiment of the present disclosure, the viral response pathway may be inappropriately not activated or improperly activated during a viral infection, such as CIVD-19 infection.

The activation of the bacterial/fungal/physical damage response pathway (FIG. 2) or the viral response pathway (FIG. 3) of the renin-angiotensin system is dependent on context. Trauma or inflammation sensed by TRPv1 mediated stretch receptors signals via the vagus nerve to respond to trauma or a large scale bacterial infection. However, SARS-CoV-2 and other pathogens may dysregulate the renin-angiotensin system by hijacking the bacterial/fungal response pathway and inhibiting the viral response pathway, as shown in FIG. 4. FIG. 4 is a schematic illustration of the incorrect extracellular pathogen signaling of SARS-CoV-2, which leads to inhibition of the inflammation negative feedback loop. SARS-CoV-2 infection is associated with ACE2 inhibition, an artificial angiotensin II increase, and downregulation of the anti-inflammation response. Further, infected cell responses that promote cell death in infected cells are not downregulated to limit effects in non-infected cells, leading to wider cell death.

Figure 5:
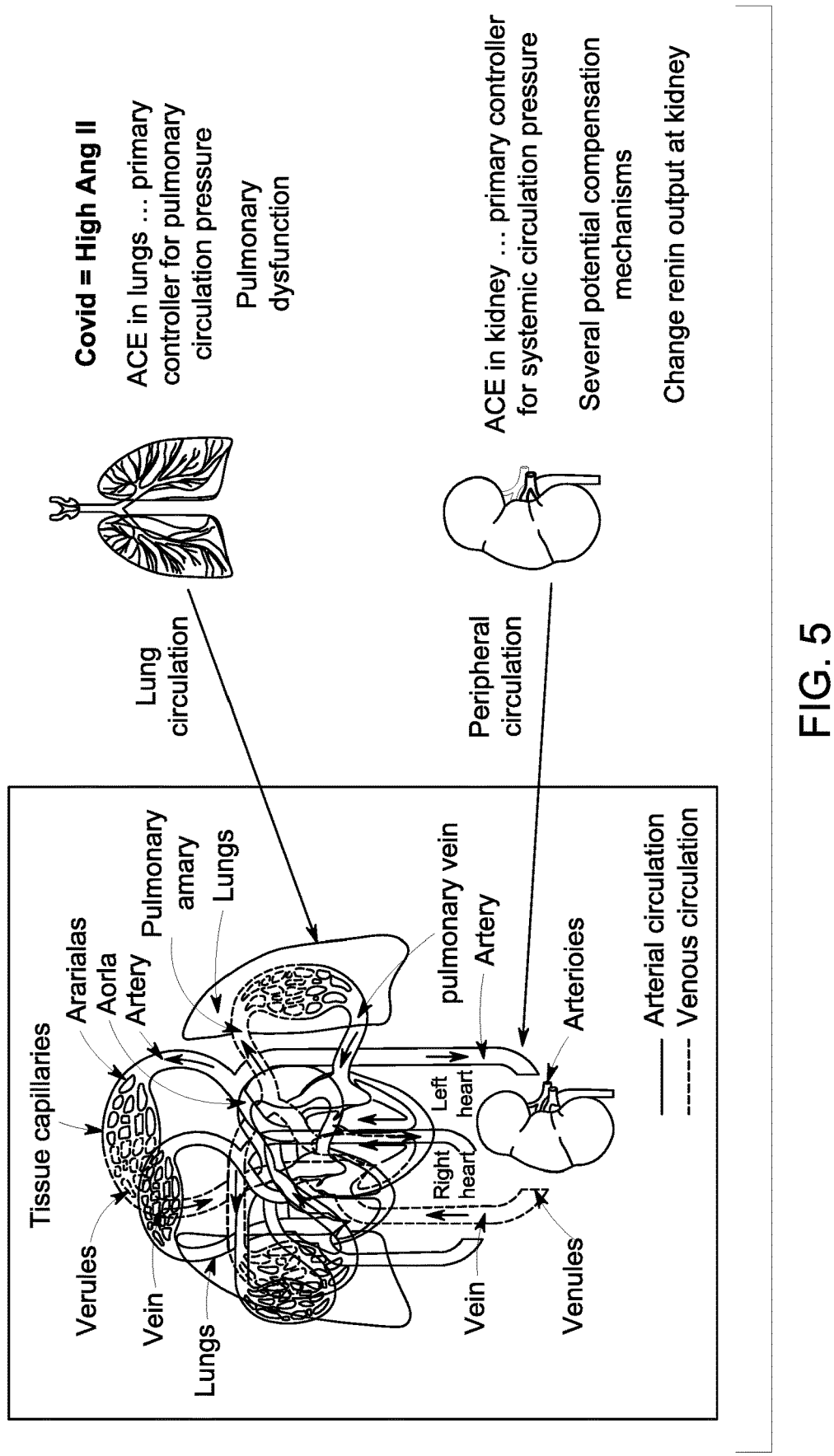
FIG. 5 is a schematic illustration of a dysregulated trauma regulation pathway in the lungs in the context of SARS-CoV-2 infection in accordance with embodiments of the disclosure.
Figure 6:
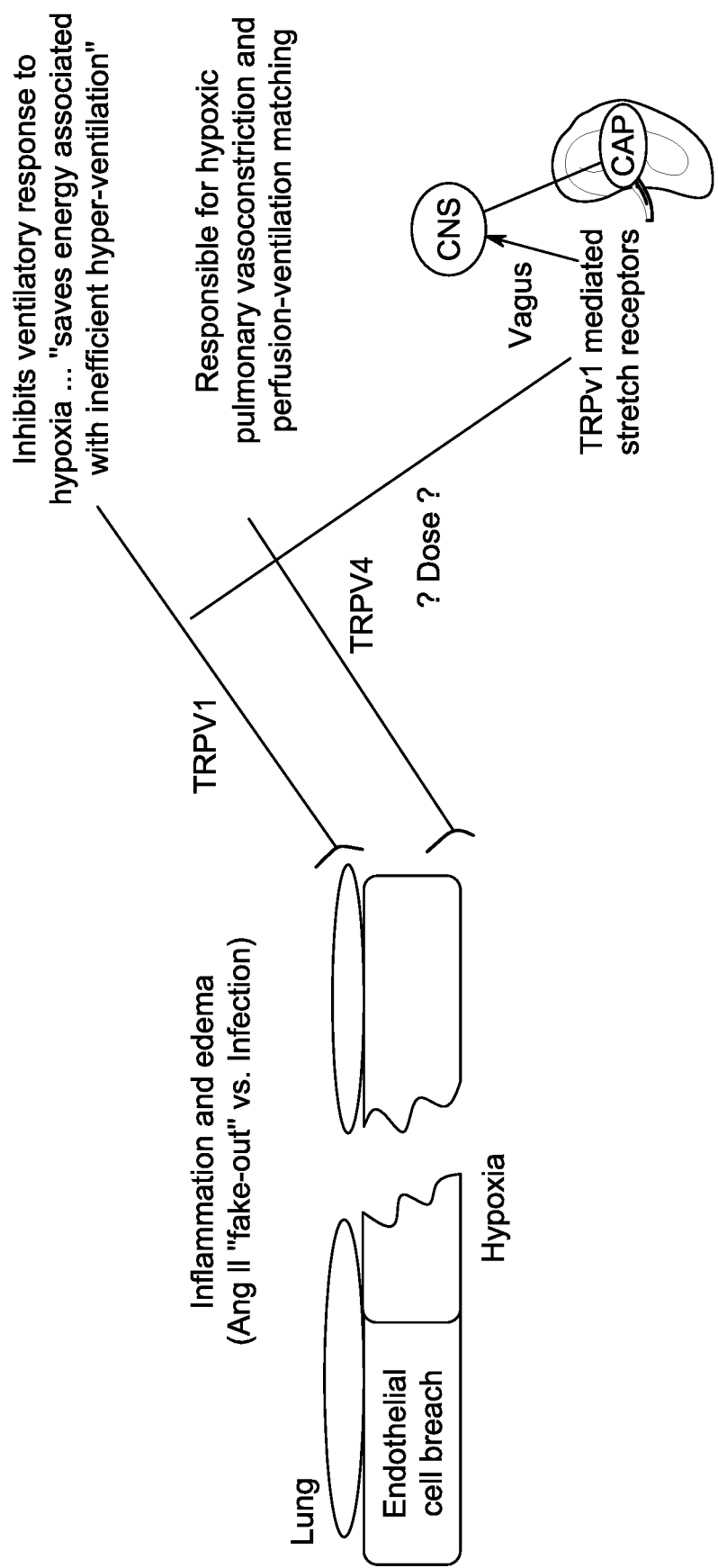
FIG. 6 is a schematic illustration of a dysregulated trauma regulation pathway hypoxia response in the context of SARS-CoV-2 infection in accordance with embodiments of the disclosure.
Figure 7:
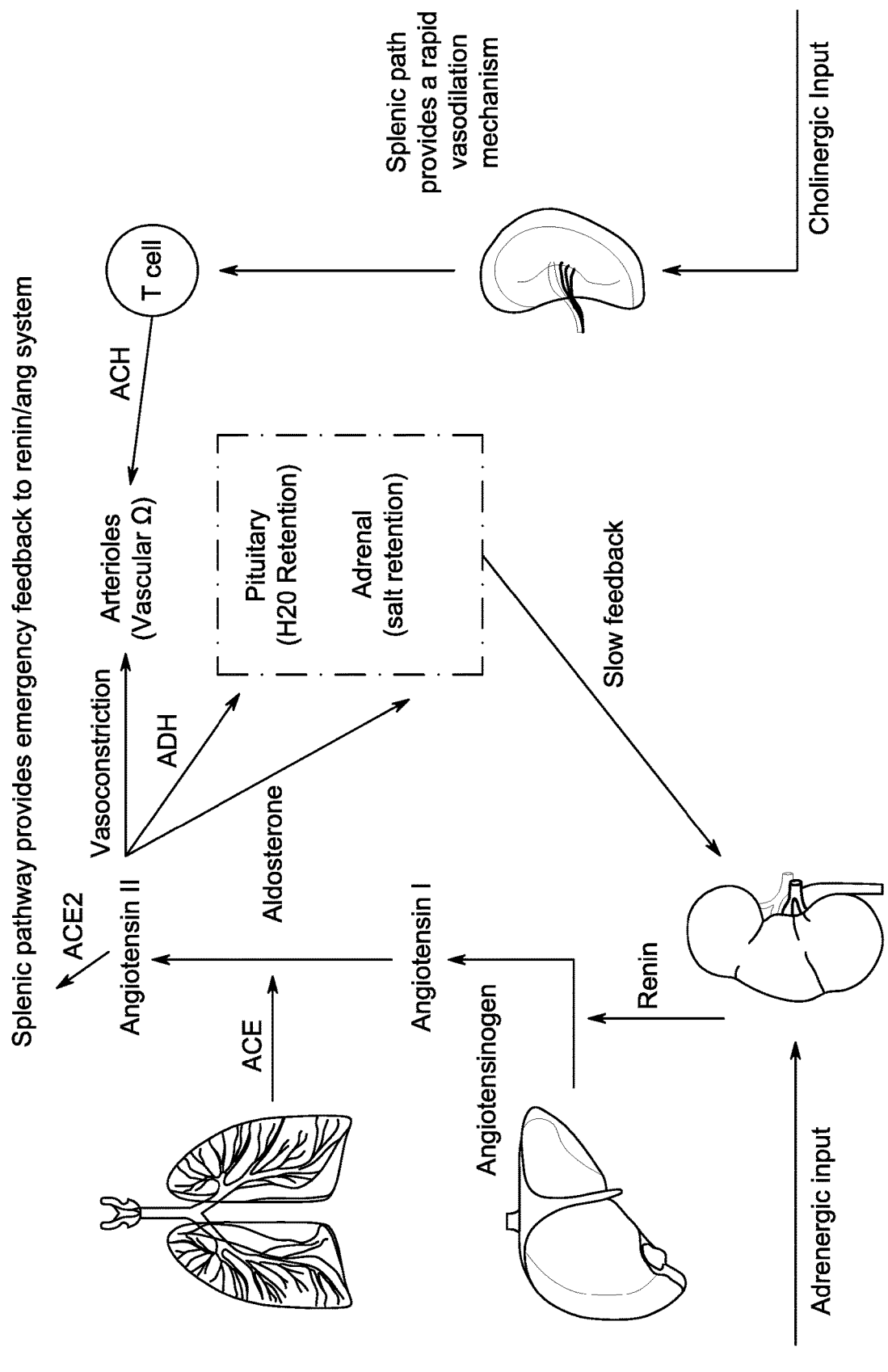
FIG. 7 is a schematic illustration of feedback activating a splenic side of a trauma regulation pathway in accordance with embodiments of the disclosure.
Figure 8:
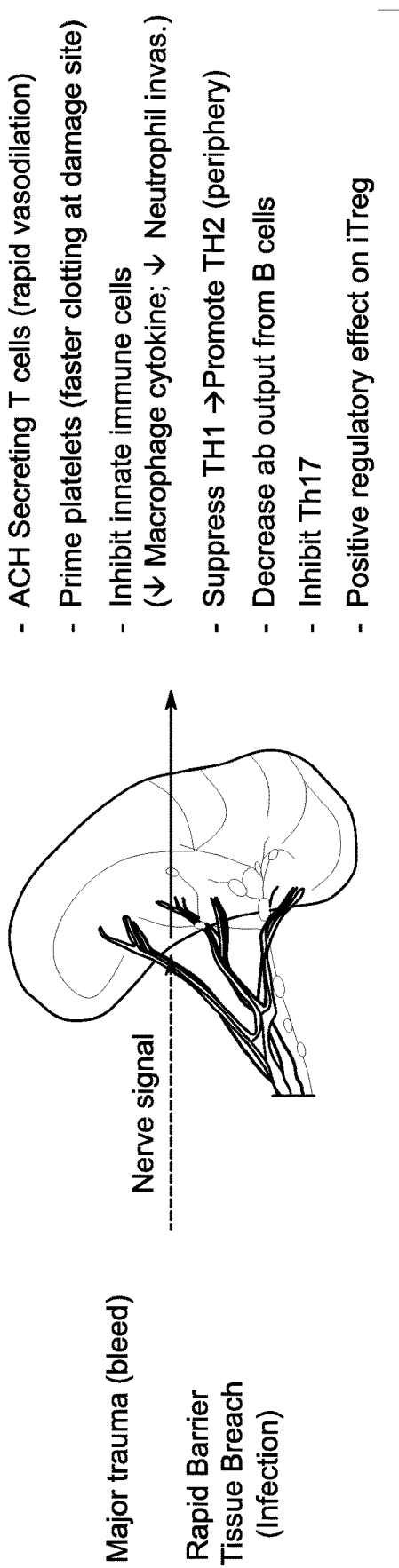
FIG. 8 is a schematic illustration of signaling to activate the splenic side of a trauma regulation pathway in accordance with embodiments of the disclosure.
Figure 9:
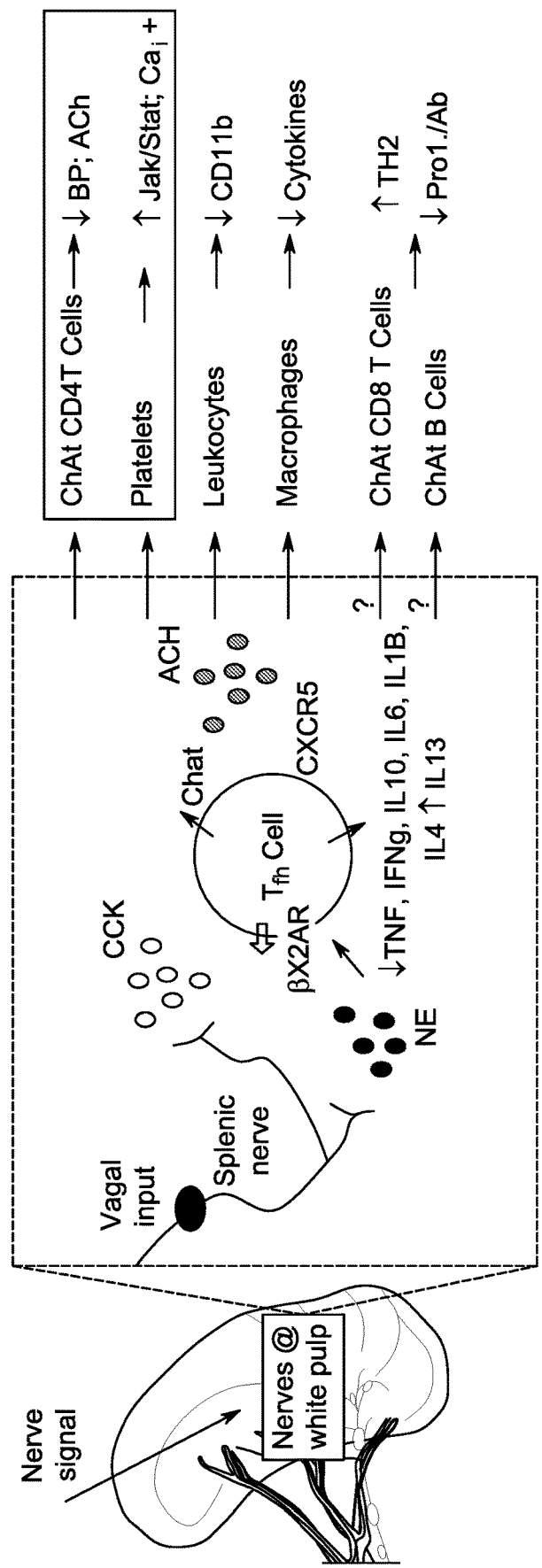
FIG. 9 is a schematic illustration of effects of the activated splenic side of a trauma regulation pathway in accordance with embodiments of the disclosure.
Figure 10:
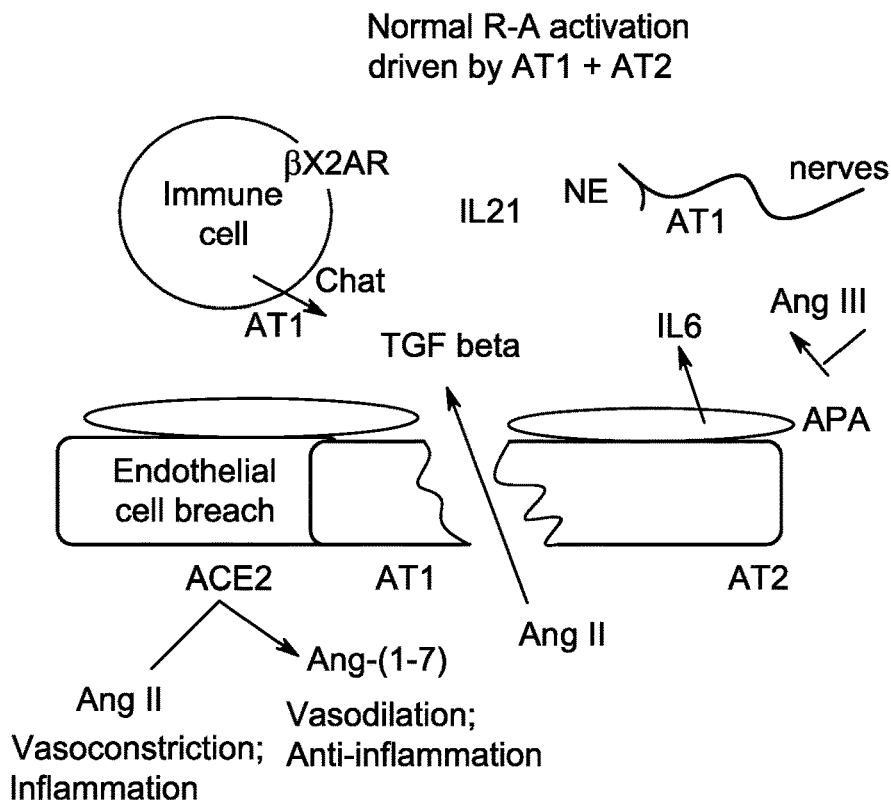
FIG. 10 is a schematic illustration of signaling to activate the renin-angiotensin system of a trauma regulation pathway in accordance with embodiments of the disclosure.
Figure 11:
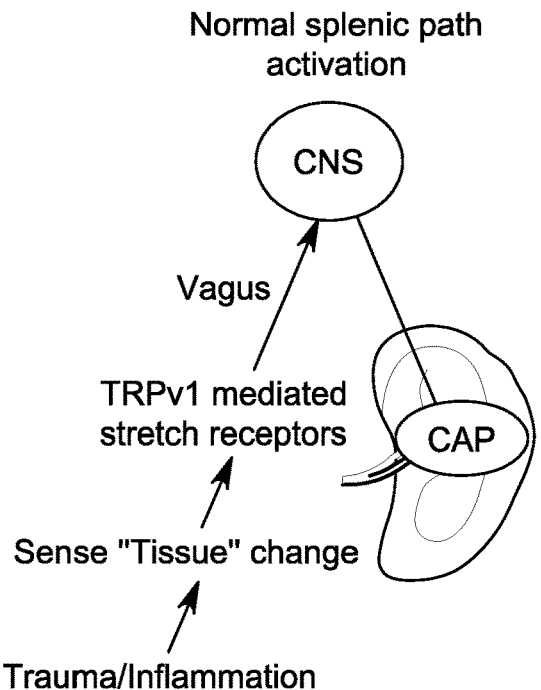
FIG. 11 is a schematic illustration of neural signaling to activate the splenic side of a trauma regulation pathway in accordance with embodiments of the disclosure.
Figure 12:
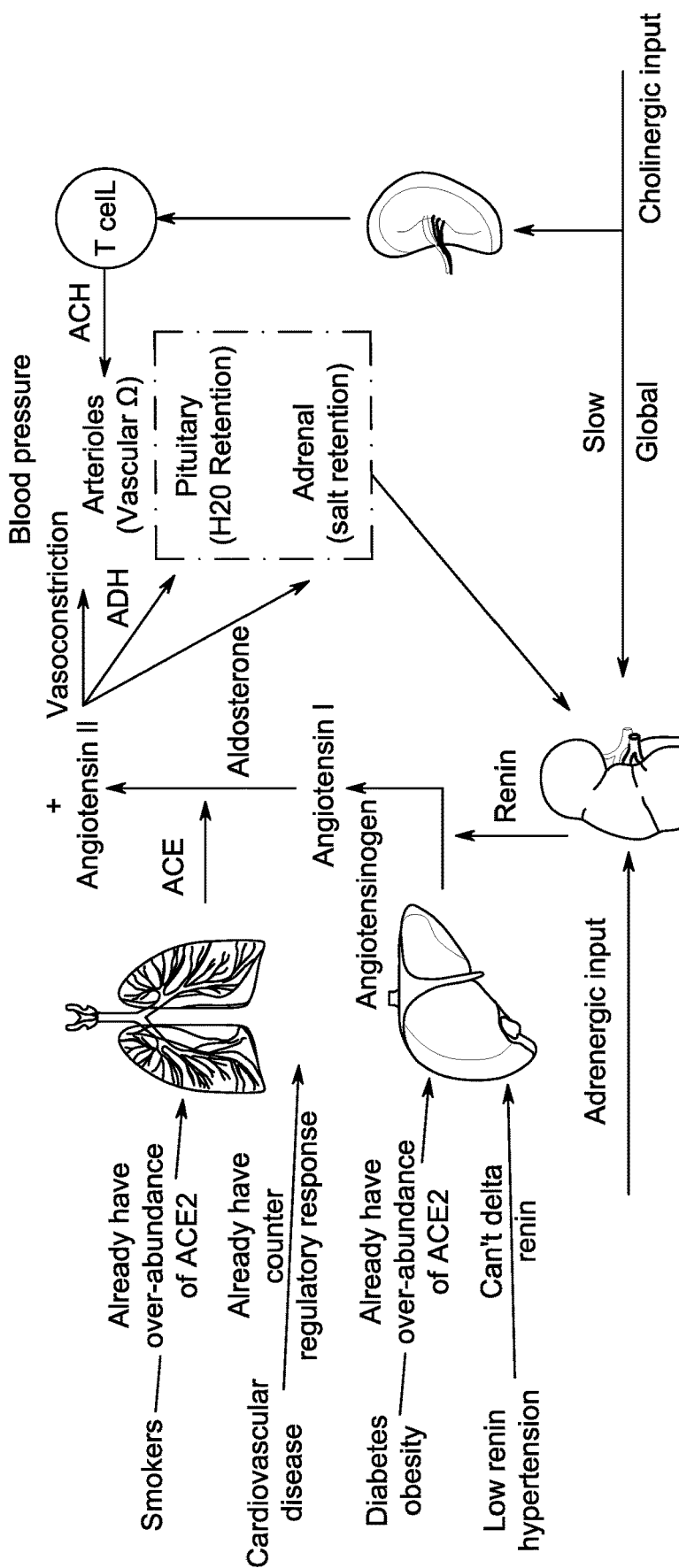
FIG. 12 is a schematic illustration of a dysregulated trauma regulation pathway hypoxia response in the context of SARS-CoV-2 infection for patients with co-morbidities in accordance with embodiments of the disclosure.
Figure 13:
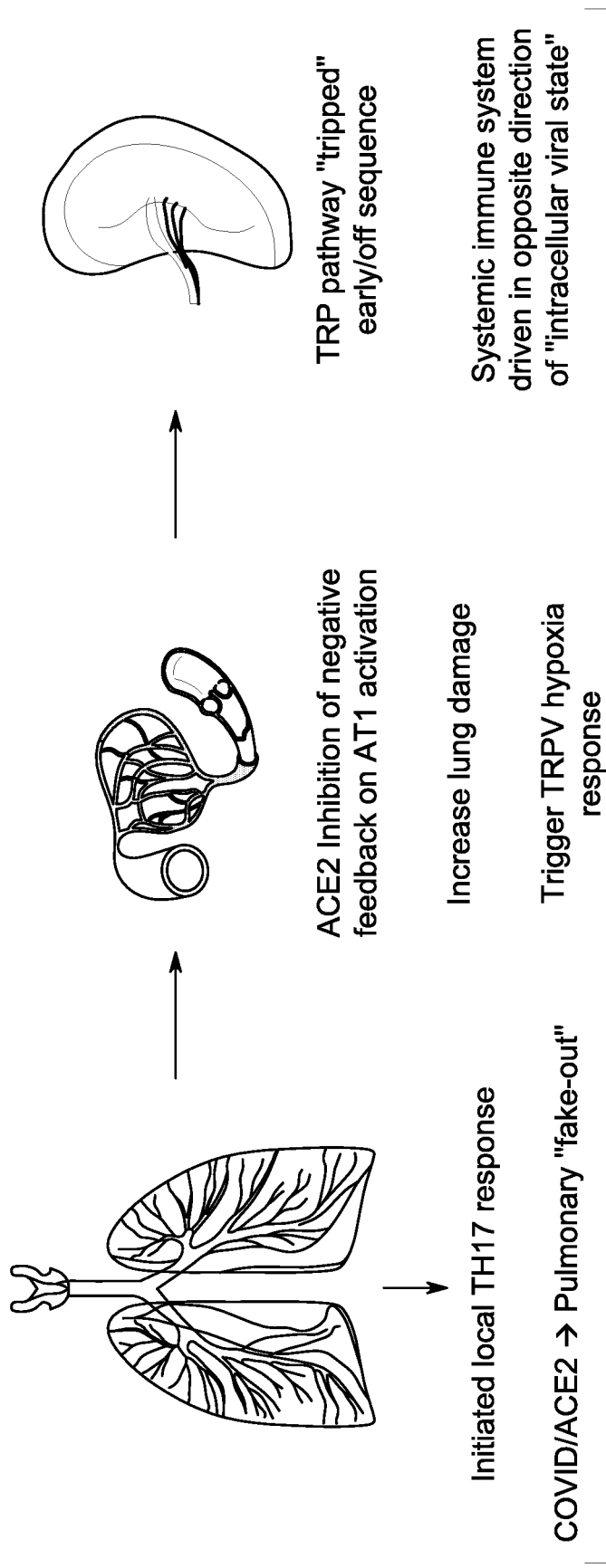
FIG. 13 is a schematic illustration showing an interplay between a lung infection and the splenic response pathway in accordance with embodiments of the disclosure.

FIG. 5 shows the effects of trauma regulatory pathway dysregulation of SARS-CoV-2 in the lungs as a result of the artificially high angiotensin II concentrations, which may be the result of hijacked signaling to push the renin-angiotensin system to a bacterial response profile. Because this suite of physiological countermeasures in response to the SARS-CoV-2 infection is not aligned with the effects of viral infection in the cells, the body cannot respond effectively to the viral infection. Further, the negative feedback loops are interrupted, leading to cell damage and other undesirable clinical effects.

ACE in the lungs is a primary controller of pulmonary circulation pressure, and ACE in the kidney is a primary controller for systemic circulation pressure. Because of the high angiotensin II effect (related to ACE2 inhibition) in SARS-CoV-2 together with the local hypertension, SARS-CoV-2 infection may lead to pulmonary edema much earlier than other infections. The edema resembles a physical damage-induced edema rather than a viral-induced edema.

FIG. 6 is a schematic illustration of a lung role of TRPV in regulating the respiratory response to hypoxia in SARS-CoV-2 infection. TRPV1 inhibits the ventilator response to hypoxia as a result of the signaling associated with a tissue breach/wound, and TRPV4 is responsible for hypoxic pulmonary vasoconstriction and perfusion-ventilation matching. As provided herein the TRPV stretch receptors signal via the vagus nerve to act on the cholinergic anti-inflammatory pathway, which may counterbalance dysregulation of the renin-angiotensin pathway.

FIG. 7 is an overview of the rapid feedback of the splenic pathway to the renin-angiotensin system as well as the slow feedback of the kidney, which produces renin. Provided herein are treatments and/or monitoring techniques that harness the splenic responses to one or more activated pathways of the renin-angiotensin system. In one embodiment, a hyperactive or hypoactive renin-angiotensin system may be identified. In another embodiment, a hyperactive or hypoactive splenic response pathway may be identified. The nerves of the innervate arteries are largely adrenergic rather than cholinergic, and the source of acetylcholine-mediated vasodilation had not been previously linked. The present disclosure provides a cholinergic rapid vasodilation mechanism via the spleen that is mediated by T cells that secrete acetylcholine in response to cholinergic input to the spleen. This acetylcholine acts in opposition to the adrenergic input of the renin-angiotensin system.

FIG. 8 is a schematic illustration showing the effects of signaling via the vagus nerve on the spleen in response to major trauma or a rapid barrier tissue breach (infection). The response may include promotion of acetylcholine secreting T cells (resulting in rapid vasodilation), prime platelets (fast clotting), inhibition of innate immune cells (decrease in macrophages, neutrophils, suppression of TH1 and promotion of TH2 in the periphery, decrease antibody production from B cells, inhibit TH17, and a positive regulatory effect on iTreg cells. FIG. 9 shows additional details of activation of the splenic pathway. In particular, the vagal input to the splenic nerve results in a pro-inflammatory response that releases norepinephrine and CCK. These in turn result regulate T cells to produce acetylcholine. Acetylcholine acts to alter the immune response in the renin-angiotensin system. In one example, the renin-angiotensin system activation is characterized by high IL21 while the activated splenic response pathway is characterized by downregulation of IL21. Further, the activation of the splenic response pathway directed to the site of renin-angiotensin activation may act in a pro-coagulant manner to stop local bleeding, and localize the immune response to prevent undesired systemic immune responses that may eventually lead to a cytokine storm or other undesired outcomes.

FIG. 10 shows a normal activation of the renin-angiotensin side of the trauma regulation pathway driven by angiotensin 1 (AT1) and angiotensin 2 (AT2) receptors to promote vasoconstriction, aldosterone and vasopressin release, sodium and water retention and sympathetic facilitation (when dominated by AT1 signaling). The switch from pro-inflammation to anti-inflammation and vasoconstriction to vasodilation is mediated by ACE2 conversion of angiotensin II to angiotensin (1-7) (and AT2 dominated signaling). AT1 receptors are present in the kidney, but are also found in other locations in the body, such as the heart and central nervous system. FIG. 11 shows the splenic response side of the trauma regulation pathway, activated by trauma/inflammation and corresponding tissue changes (e.g., TRPv1 receptors) to trigger vagus nerve signaling in the central nervous system and activation of the cholinergic anti-inflammatory pathway (CAP).

FIG. 12 shows an example of dysregulation that may occur for patients with reduced capacity to activate the renin-angiotensin system to compensate for the splenic response pathway. Such patients may include smokers, who have an overabundance of ACE2. Patients with cardiovascular disease already have an activated counter-regulatory response. Patient with diabetes or obesity exhibit increased tissue angiotensin II, and those with low renin hypertension cannot change their renin production in response. Accordingly, co-morbidities may lead to dysregulation in the renin-angiotensin pathway, and resultant undesired clinical effects, such as an increased risk of pulmonary edema. In these patients with co-morbidities, there may be inability to compensate, which may lead to early activation of the splenic regulation pathway.

FIG. 13 shows the effects of such dysregulation in the lungs in the case of SARS-CoV-2 infection. As discussed herein, the COVD-19 infection pathway may push the trauma regulation pathway towards a response that more closely resembles the tissue breach or wound response (because the virus is activating this pathway typically associated with physical damage). In turn, the lungs exhibit characteristic initiated local TH17 response, which cannot be resolved when ACE2 inhibition of negative feedback on AT1 activation and/or miss-timed activation of the TRPV hypoxia response is also taking place. The clinical results may be an increase in lung damage. Further, the splenic side of the trauma activation pathway may be triggered early, which drives the systemic immune system in the opposite direction of the characteristic or desired response associated with an intracellular viral state.

FIG. 14 is a schematic illustration showing a normal gut response pathway (top) and a gut response pathway for a SARS-CoV-2 infection (bottom). The SARS-CoV-2-associated increase in angiotensin II (and/or reduction in circulating ang I) may modulate CCK cleavage, further promoting systemic immune dysfunction. Increased angiotensin II may also drive ACE surface expression as a defense against gut invasion. ACE is the cleavage enzyme for both angiotensin I and CCK in the gut. If this occurs in a manner that activates the opposing splenic response pathway, B cell function is knocked down in the renin-angiotensin system side. If this also occurs on the splenic side of the pathway, then the patient will have severe B cell and antibody production deficits. Further, platelets are also activated and the system may become pro-thrombotic in both directions, which may cause the anomalous clotting behavior of SARS-CoV-2 infections.

Figure 15:
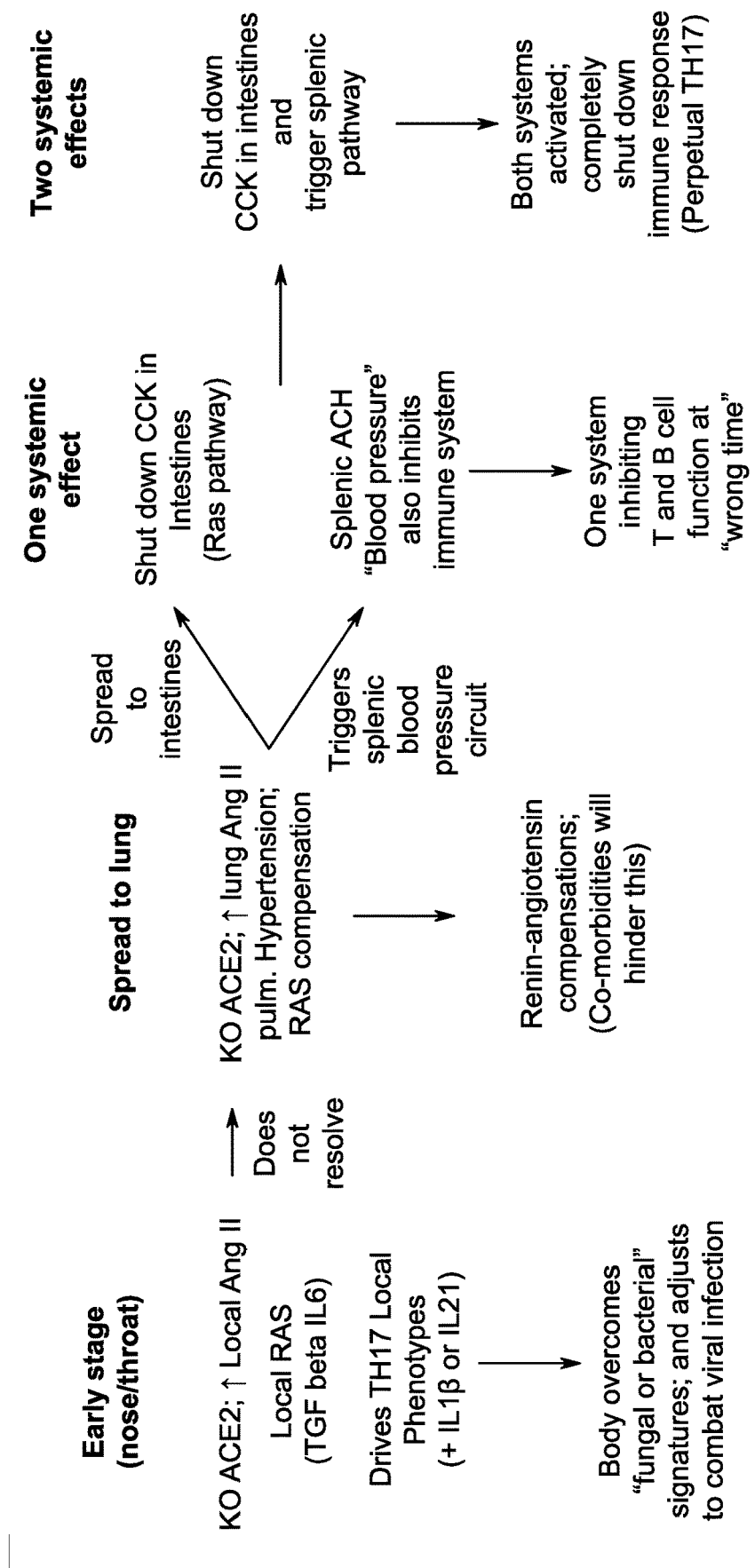
FIG. 15 is a flow path of COVID 19 infection and stage of trauma regulation pathway activation in accordance with embodiments of the disclosure.

FIG. 15 is a flow path of SARS-CoV-2 disease progression and its effects on various pathways. As provided herein, the exhibited response pathways may be used as part of diagnosis, monitoring, and/or treatment. In the early stage of infection in the upper respiratory structures (nose/throat), the response may drive activation of a local renin-angiotensin system in the upper respiratory tissues. These tissues may exhibit local ACE2 knockout or reduction and increase in local angiotensin II as well as characteristic local immune/cytokine responses driven by TH17. Angiotensin-converting enzyme (ACE) mediates the ventilator-induced inflammatory response in healthy lungs. An observed effect in SARS-CoV-2 is a positive correlation between ventilator time and mortality. In an embodiment, angiotensin II (Ang II) induces a major inflammatory response (essentially both arms of the trauma regulation pathway being simultaneously active) causing accumulation of inflammatory mediators in the lung.

Figure 14:
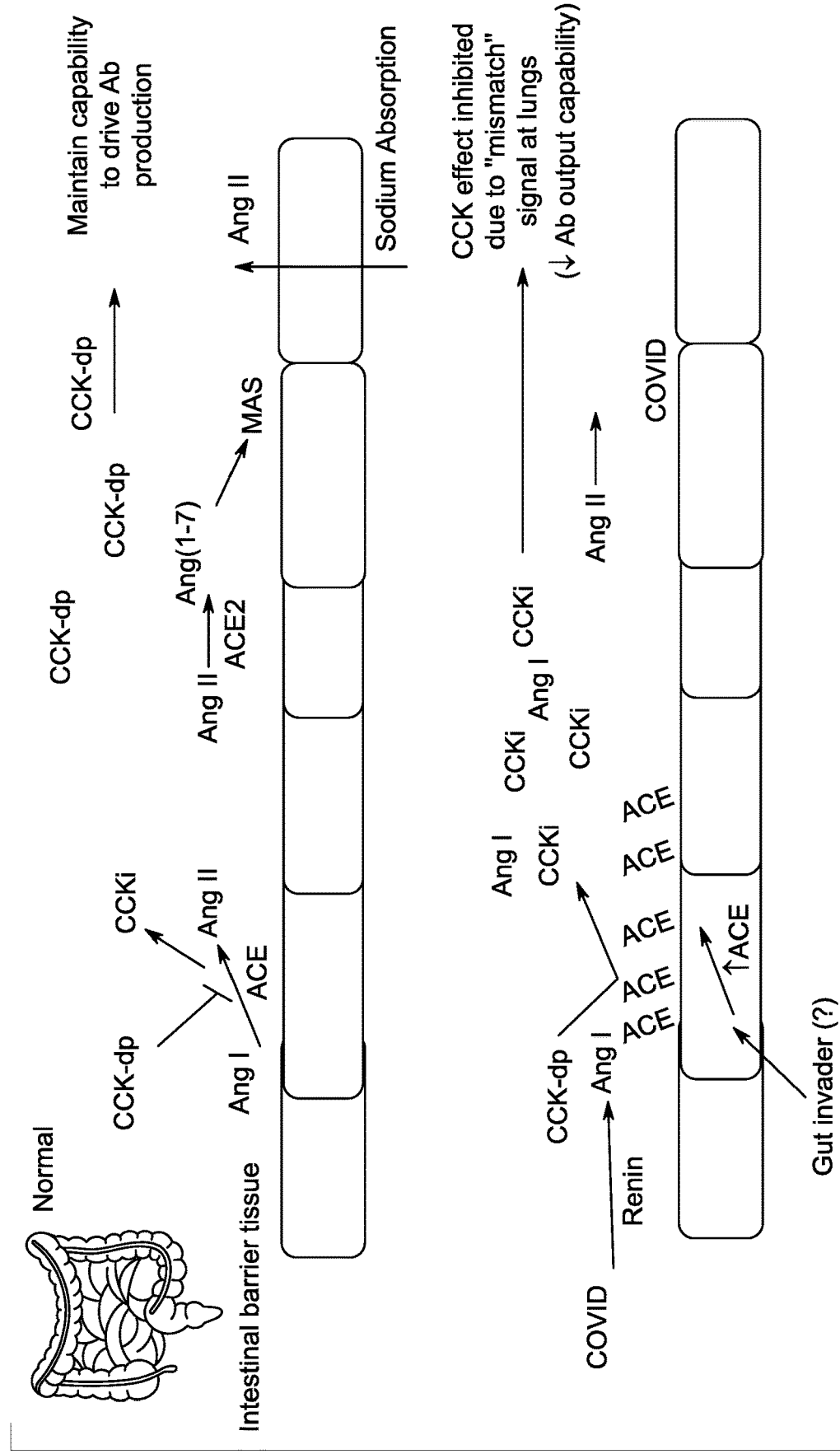
FIG. 14 is a schematic illustration of gut tissue response to the trauma regulation pathway with or without SARS-CoV-2 presence in accordance with embodiments of the disclosure.

In an embodiment, the presence of increased IL-6, TGF-beta, or IL-21 in the upper respiratory tissues may be characteristic of an early stage of infection. When or if the SARS-CoV-2 infection spreads to the lungs, the renin-angiotensin system activation compensations may cause lung angiotensin II negative feedback to local inflammation and a reduction in the hypoxia response. At some point, the splenic response pathway activation may also be activated, which in turn acts to dampen the systemic immune system and T and B cell function. Further, the SARS-CoV-2 infection may spread to the intestines (see FIG. 14). Spread of SARS-CoV-2 to additional tissue location may feed into the splenic response pathway such that the renin-angiotensin system and the splenic response pathway may both be dysregulated to shut down systemic immune response (thus perpetuating a local, non-resolved inflammatory event).

FIG. 16 shows a summary of SARS-CoV-2 therapies that, according to embodiments, may be administered with timing governed by a stage of infection. As provided herein, the stage of infection may be determined by assessing a presence or concentration of characteristic factors (e.g., molecules). In an embodiment, an ACE inhibitor administration may be timed to be in conjunction with an early stage of infection and not in later stages to avoid tripping an immune inhibition pathway. IL-6 knockdown drugs may be more effective at later stages by checking the TH17 phenotype. However, the presence of IL-21 may be compensatory and may limit the effectiveness of IL-6 knockdown. Accordingly, IL-21 knockdown drugs (or combinations) may be more effective. Administration of anti-virals may not prevent the renin-angiotensin dysregulation, if given too late in disease progression. Accordingly, anti-viral administration may be performed in conjunction with monitoring of one or more molecules of the renin-angiotensin system. In an embodiment, methods of treating SARS-CoV-2 with angiotensin receptor antagonists (AT1 receptor antagonists) is provided. The treatment may prevent activation or modulation of the splenic pathway. The administration may be timed to occur if/when SARS-CoV-2 enters the lungs to prevent local immune reaction in the upper respiratory tissues. Further, administration may be in conjunction with monitoring of the splenic pathway. Administration may be timed to presence of SARS-CoV-2 in the lungs and before the splenic pathway is activated. Accordingly, administration may be in conjunction with monitoring one or more molecules of splenic pathway activation. In an embodiment, the treatment is a CCK antagonist to drive immunostimulation and in conjunction with monitoring of one or more immune molecules to assess immune response and whether an antiviral or antibacterial pathway is active.

Figure 17:
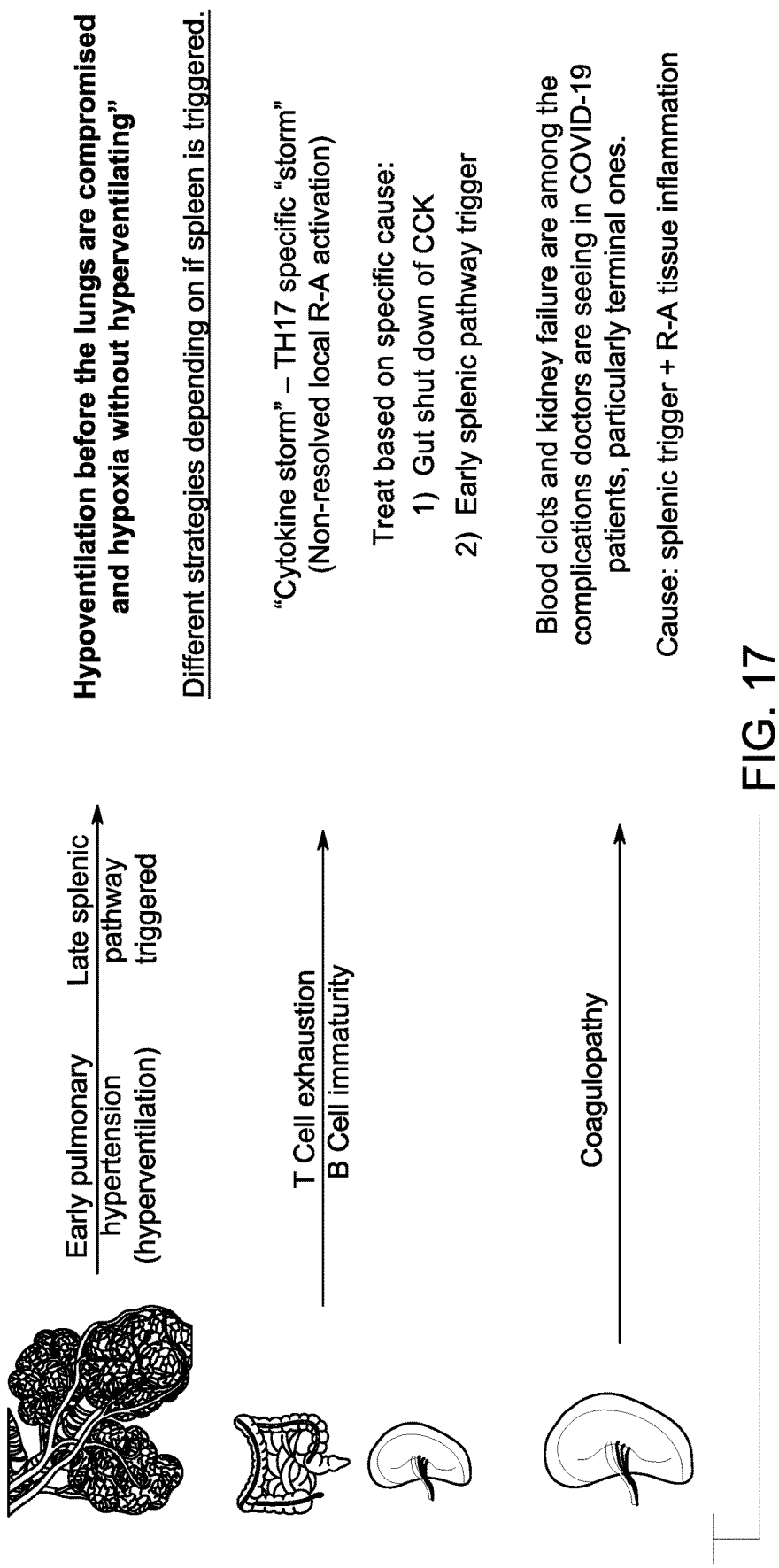
FIG. 17 shows overall effects of SARS-CoV-2 on the trauma regulation pathway in accordance with embodiments of the disclosure.

FIG. 17 shows certain effects of SARS-CoV-2 induced dysregulation in the trauma regulation pathway. In one example, patients exhibit early pulmonary hypertension and hyperventilation. Treatment may be based on assessment of the status of the splenic pathway. For patients with immune responses such as T cell exhaustion and B cell immaturity, treatment may be based on whether there is a gut shutdown on CCK and/or a sign of an early splenic pathway triggering. For patients with coagulopathy, the root cause may be splenic trigger and renin-angiotensin tissue inflammation. Treatments to reduce splenic effects may be effective.

Figure 18:
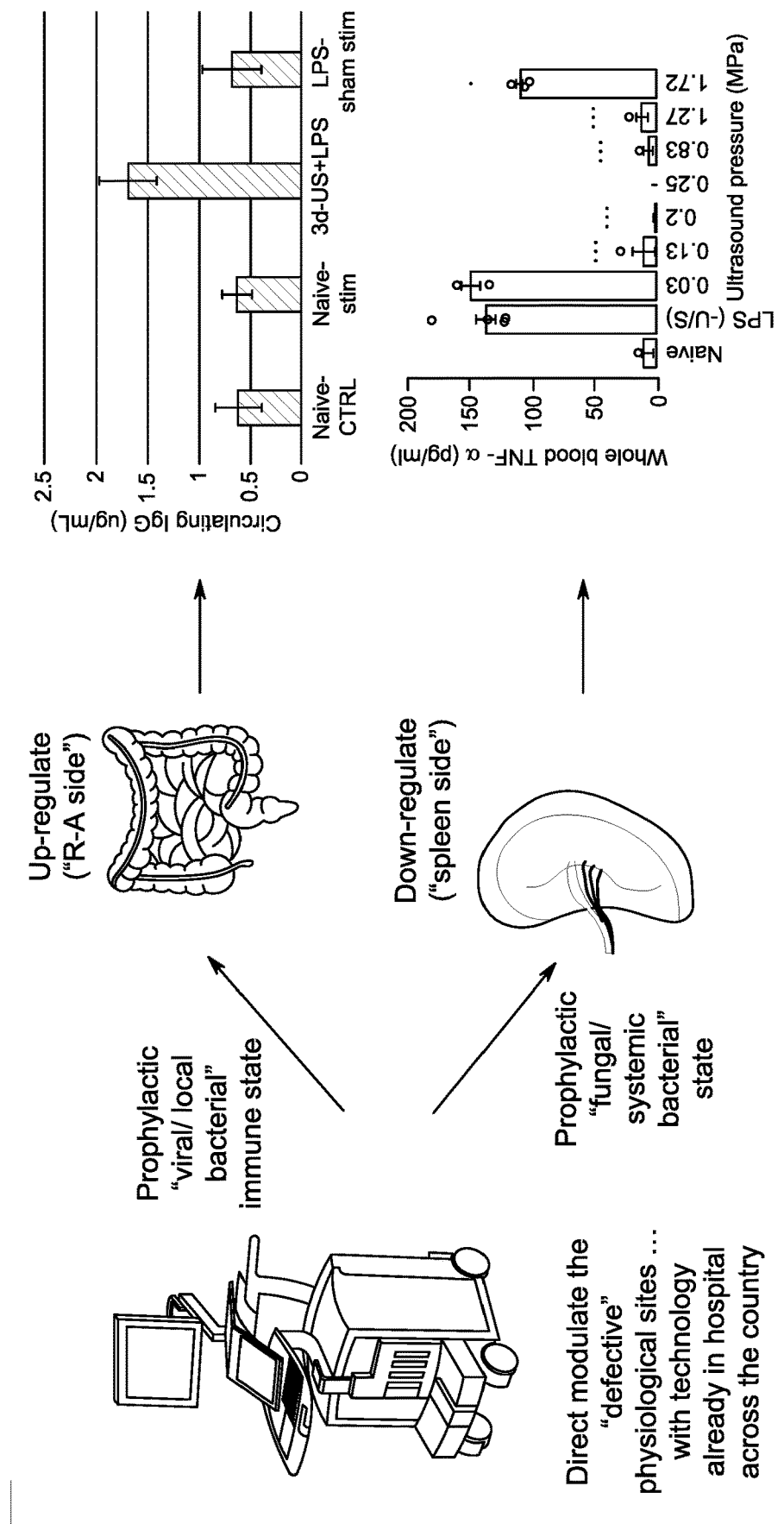
FIG. 18 is a schematic illustration of effects of neuromodulation on the trauma regulation pathway in accordance with embodiments of the disclosure.

FIG. 18 is a schematic illustration of an embodiment of a neuromodulation therapy to treat dysregulation of the trauma regulation pathway. In an embodiment, focused ultrasound energy is applied to a gastrointestinal tissue to inhibit inactivation of B cells on renin-angiotensin system side.

Provided herein are techniques that use applied ultrasound energy to cause a modulation of the immune response. In embodiments, the modulation is a treatment of subjects infected with a pathogen. In embodiments, the applied ultrasound energy is used as an adjuvant to boost the effectiveness of a vaccine or treatment.

For certain subjects, infection (e.g., SARS-CoV-2 infection) causes an innate immune response that is too active and that may result in collateral damage to uninfected cells. Accordingly, ultrasound energy application to targeted tissues, such as the spleen or lymph tissues (e.g., a lymph node), via externally-applied energy, triggers activation of nerve/signaling pathways that help shut down an overactive innate immune response but, in some cases, also may cause an associated increase in an adaptive immune response. These responses may be tracked by proxy immune markers of innate and/or adaptive immune responses to set desired endpoints for the neuromodulation as discussed herein. In one example, a desired endpoint is a prognostic score based on the ratio of IL-6 to IL-IL-10, which is an inflammatory cytokine balance of a more pro-inflammatory cytokine (IL-6) to that of a more anti-inflammatory and pro-resolution cytokine IL-10. The ratio may be calculated as generally set forth in McElvaney, O. J et al. (2020). *A linear prognostic score based on the ratio of interleukin-6 to interleukin-10 predicts outcomes in SARS-CoV-2*. EBioMedicine, 61, 103026, which is incorporated by reference herein. In an embodiment, a subject with an elevated IL-6, e.g., above 80 pg/mL, is considered to have an inappropriately elevated innate immune response and is selected for treatment, while IL-6 levels below 80 pg/ML or below 50 pg/ML in a subject are not indicative for treatment. In an embodiment, a subject with an a Dublin-Boston score of 1 or 2 is selected for treatment and scores of 0, −1, or −2 are not selected for treatment. Accordingly, in one example, a subject's ratio of IL-6:IL-10 is tracked at baseline and after neuromodulating energy is applied to the spleen/lymph tissue. Decreases in IL-6 and concurrent increases in IL-10 may be associated with desired neuromodulation treatment endpoints. In an embodiment, the score is a Dublin-Boston score, whereby a decrease in the score relative to baseline is associated with desired treatment endpoints. In an embodiment, the score is a Dublin-Boston score, whereby a score of 0, −1, or −2 after neuromodulating treatment is associated with desired treatment endpoints.

In certain embodiments, tissue targets for neuromodulation, such as gastrointestinal (GI) tissue or the liver, may additionally or alternatively be selected to boost adaptive immune responses in conjunction with the spleen/lymph node targeted neuromodulation to decrease innate immune response. Thus, as provided herein, targeted application of ultrasound energy can be used to shift the body's response from innate to adaptive immunity.

Figure 19:
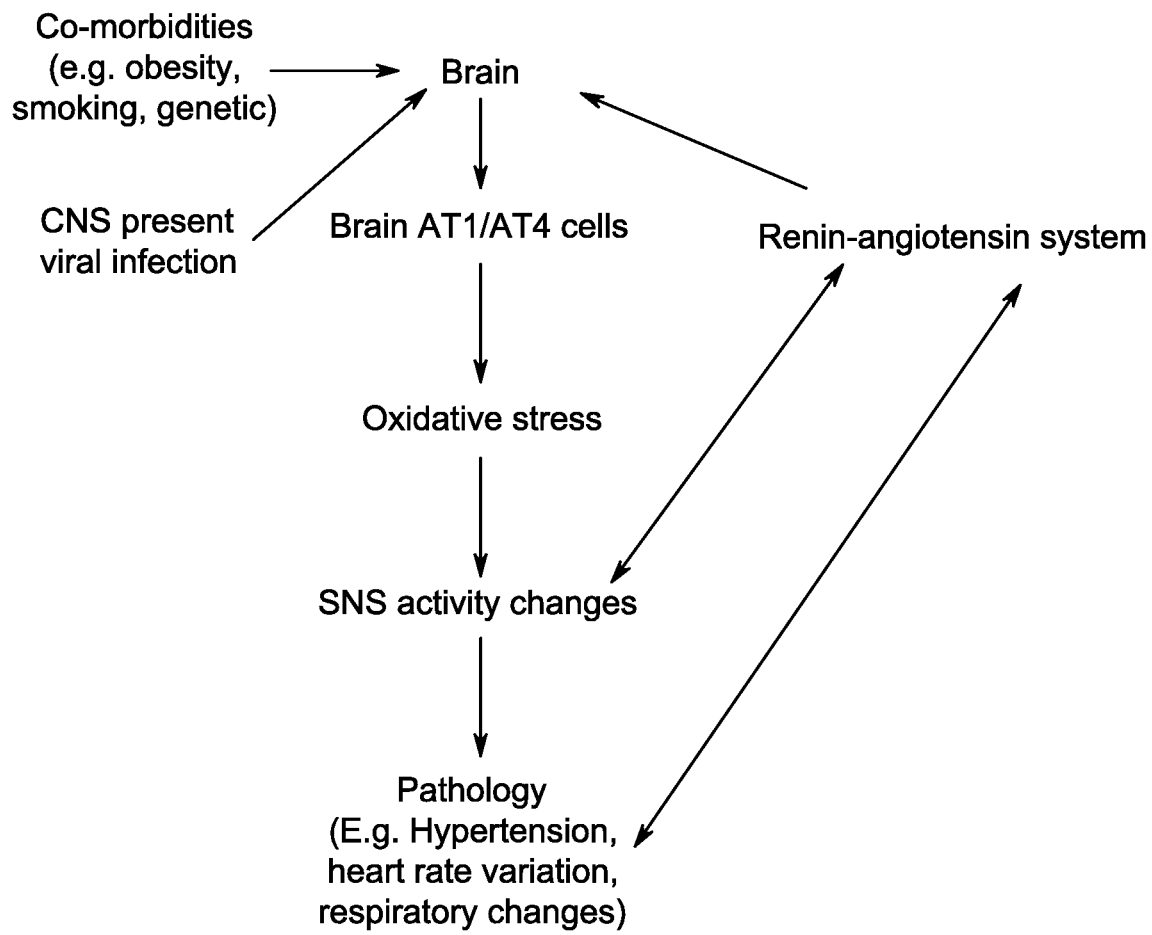
FIG. 19 is a schematic illustration showing that the renin angiotensin system is mediated to some extent by the brain.
Figure 20:
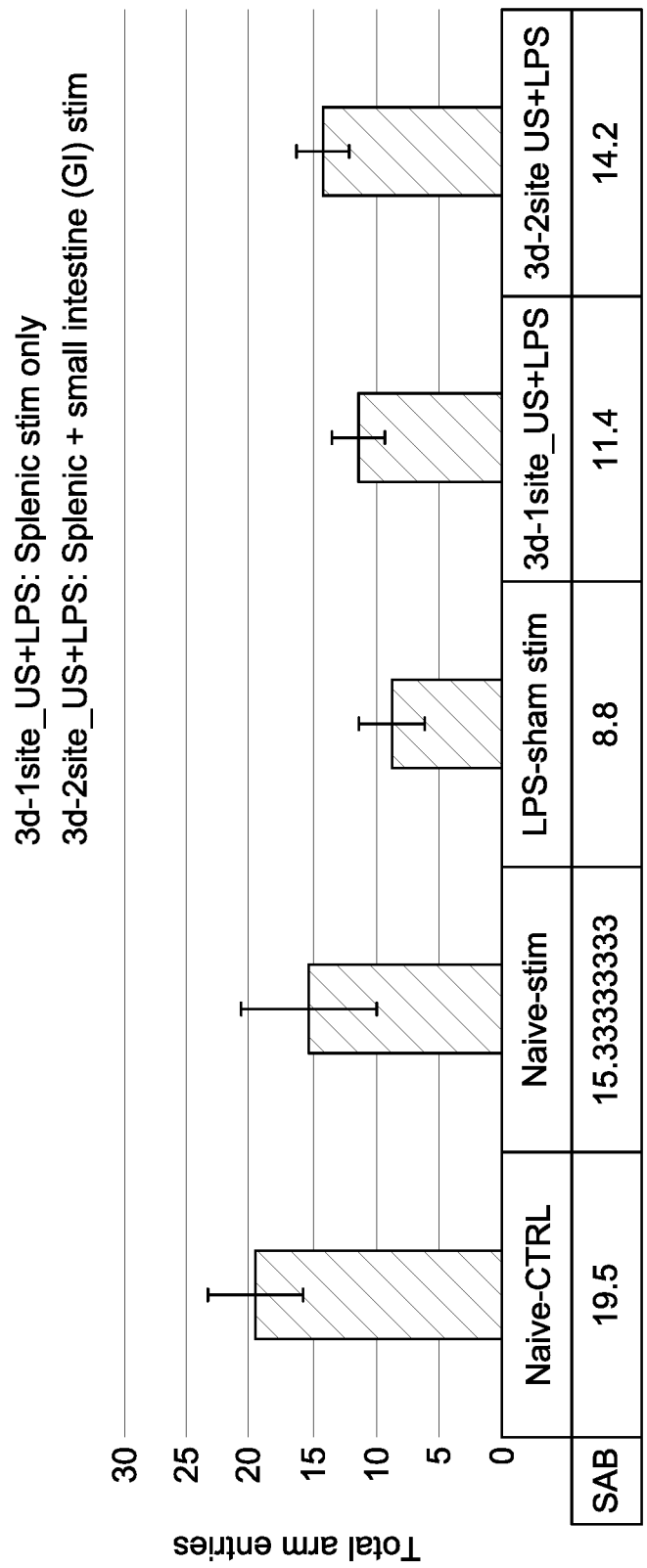
FIG. 20 shows the effects of cytokine storm in an animal model on measured rodent locomotion.
Figure 21A:
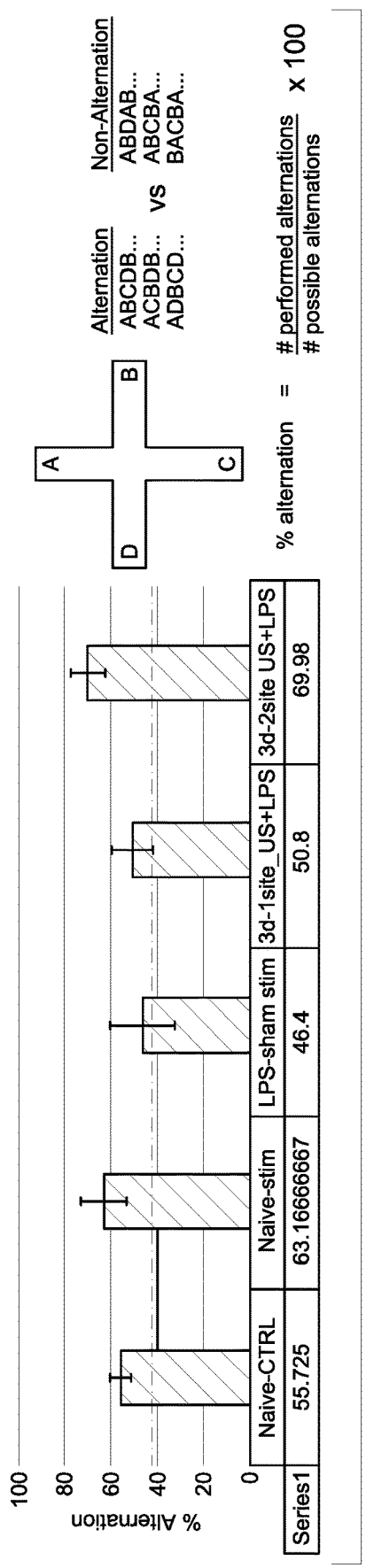
FIG. 21A shows the effects of cytokine storm on spatial working memory.
Figure 21B:
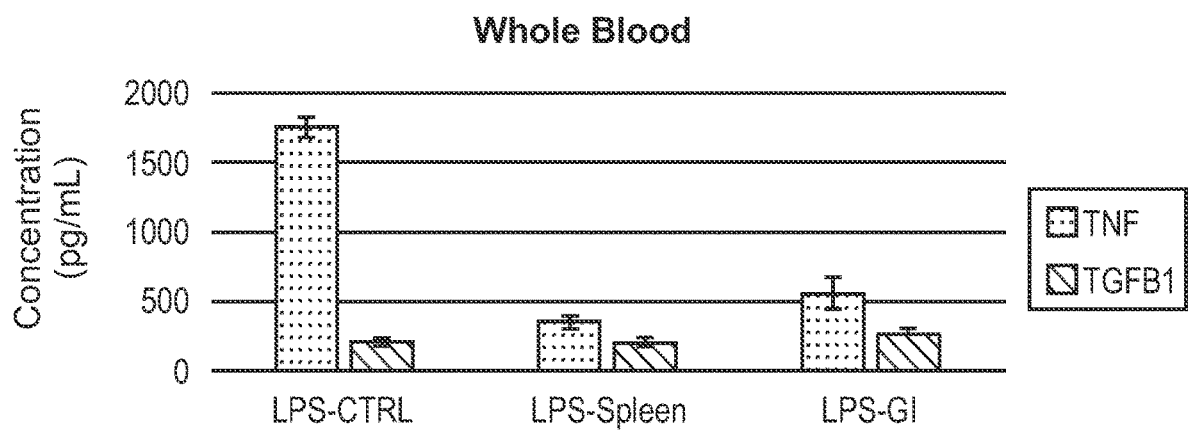
FIG. 21B shows whole blood concentrations of TNFα and TGF-β1 in ultrasound-stimulated and LPS-treated animals for spleen and gastrointestinal treatment sites.
Figure 21C:
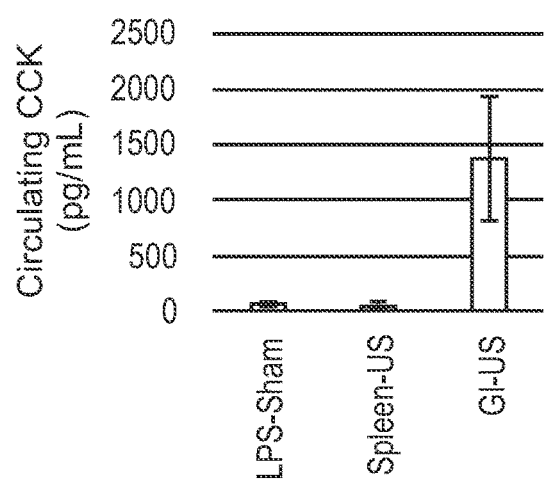
FIG. 21C shows circulating CCK-8 concentrations in ultrasound-stimulated and LPS-treated animals for spleen and gastrointestinal treatment sites.
Figure 21D:
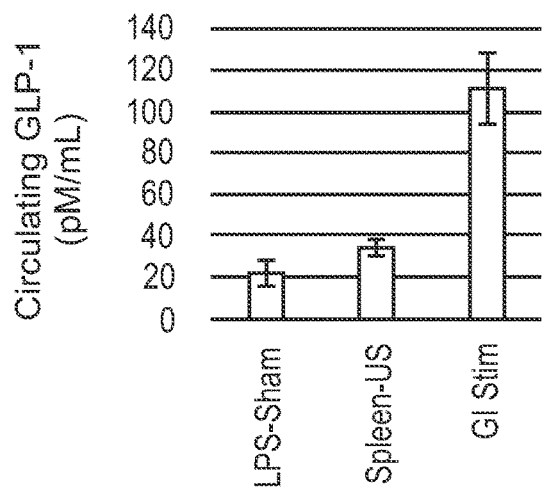
FIG. 21D shows circulating GLP-1 concentrations in ultrasound-stimulated and LPS-treated animals for spleen and gastrointestinal treatment sites.
Figure 21E:
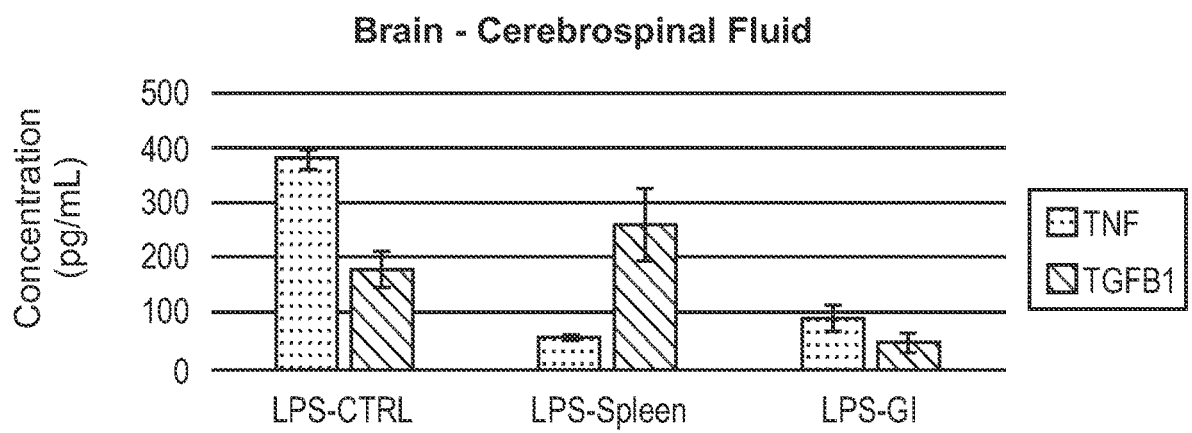
FIG. 21E shows brain-cerebrospinal fluid concentrations of TNFα and TGF-β1 in ultrasound-stimulated and LPS-treated animals for spleen and gastrointestinal treatment sites.

It should be understood that brain or CNS effects may contribute to both sides of the trauma regulation pathway. FIG. 19 shows that the renin angiotensin system is mediated to some extent by the brain.

Viruses, including those in the beta-CoV class (SARS, MERS, HCoV-229E, HCoV-0C43) do not remain confined to the respiratory tract and may invade other peripheral tissues and the CNS, inducing a myriad of disease. However, the beta-CoV virus may infect a human host by binding to the angiotensin converting enzyme 2 (ACE2) cellular receptor, which is expressed in alveolar epithelial cells and parenchyma of the lung, vascular endothelia of the circulation, enterocytes of the small intestine, neurons of the brain and the tubular and glomerular epithelial cells of the kidney. However, the presence of ACE2 or DPP4 solely is not sufficient to make host cells susceptible to infection, nor is it alone sufficient to induce significant symptomology. Other viruses and pathogens may also act through the trauma regulation pathway in other ways to dysregulate the immune system, contributing to cytokine storm and/or sepsis.

Patients with SARS demonstrate an elevated presence of SARS-CoV particles exclusively in neurons of various brain regions, including the hippocampus, hypothalamus and brainstem (observed post-mortem). However, the virus particles have been observed in the cerebral spinal fluid (CSF) of surviving patients. Rodent studies confirmed that when exposed intranasally, prior CoV viruses (e.g. SARS-CoV, MERS-CoV) enter the brain, likely through the olfactory nerve and spreads rapidly to other brain regions, following the initial inoculation. Results from these rodent studies demonstrated that low inoculum doses of SARS or MERS-CoV were detected exclusively in the brain, and not the lung. These results may indicate that infection of beta-CoV viruses in the CNS is highly correlative with mortality. In addition to direct viral impact, the brain is known to be affected by both elevation in systemic angiotensin 2 as well as chemical signals including cytokines from the splenic system, TGF-beta from the lung and cholecystokinin from the gut. CNS inhibition may also directly lead to dysregulation in peripheral nerve firing, including dysregulation of the splenic side of the trauma regulation pathway.

To investigate the effect of cytokine storm on neural functions such as loco-motion and cognition, rodents were run through a spontaneous alternation behavioral (SAB) maze which measures rodent locomotion (indicated as total arm entries, FIG. 20) and spatial working memory (indicated as % alternation, FIG. 21). Following induction of a cytokine storm by lipopolysaccharide (LPS), untreated rodents showed a significant decrease in total arm entries which was only reversible with stimulation of the splenic and gastrointestinal systems. No significant change in locomotion was observed with stimulation of the spleen alone (FIG. 20). Similar results were seen with spatial work memory where stimulation of the splenic and gastrointestinal systems showed a significant attenuation of the observed cognitive impairment (FIG. 21). Taken together these results suggest that hormonal or neural signaling from the GI tissue may attenuate the negative effects of cytokine storm on the CNS, stimulation of the splenic and subsequent reduction of circulating cytokines alone proves insufficient.

Both spleen and GI targeted stimulus via focused ultrasound (FUS) were demonstrated as decreasing circulating TNFα concentration in the blood in an animal model with induced systemic inflammation via LPS relative to a control as shown in FIG. 21B. No effect of liver stimulus was observed. No significant peripheral effect was observed with TGF-β1. However, central TGF-β1 (FIG. 21E) was elevated in LPS-CTRL animals, an effect that was not alleviated by splenic FUS targeting peripheral nerves. However, TGF-β1 was significantly reduced following stimulus of the mesenteric plexus of the GI. TGF-β1 is elevated in patients with cognitive impairments such as that observed in delirium following infection or even AD patients, and cognitive effects may be associated with the presence of neuroinflammation. GI tissue expresses CCK-8, which has been shown to reduce TNFα. GLP-1 has been shown in diabetics (by GLP-1 agonist drugs) to reduce inflammation. GI stimulus can both increase GLP-1 (FIG. 21D) in the circulation as well as increasing CCK-8 (FIG. 21C). Accordingly, embodiments provided herein are directed to using neuromodulation, e.g., via focused ultrasound, to reduce cognitive impairments associated immune responses to pathogen infection. In an embodiment, neuromodulation according to techniques disclosed herein is applied to a GI tissue, e.g., the mesenteric plexus, as a treatment for pathogen infection to ameliorate cognitive impairments.

Activation of nerves and stimulated release of neurotransmitters within local immune organs (i.e. a specific lymph node) results in transient retention of specific immune cells (i.e. lymphocytes and neutrophils) at that location. Furthermore, stimulation results in distal signaling to other immune organs (i.e. spleen and liver), transient changes in neurotransmitter concentrations at those locations, and mobilization of immune cells into circulation. Within hours of vaccination, antigen is transported to the draining lymph nodes and spleen. In an embodiment, neuromodulation targeting the lymph node or spleen can be used for a desired modulation effect, which may be one or both of up-regulation or downregulation, of the induced immune response. The neuromodulation can be applied concurrently with or during the body's immune response to vaccination. Specifically, stimulation of the lymph node directly adjacent to the location of vaccine delivery could induce a more robust response. In contrast, splenic ultrasound stimulation, which is effective in reducing disease severity in a mouse model of inflammatory arthritis, could be used to decrease the induced immune response. Lymph node stimulation by ultrasound ca be used, according to embodiments of the disclosure to increase the efficacy of vaccines to act as an energy-based or extracorporeal adjuvant. Splenic stimulation could be used to reduce the immunogenicity of treatments. In one example, side effects may be reduced. Lymph node stimulation could potentially enable a partially protective vaccine to become fully protective without requiring boosters. Splenic stimulation could allow use of drugs or treatments in people that would otherwise induce an unwanted immune response. In one example, the disclosed neuromodulation techniques can be used to boost an immune response conjunction with vaccination. Thus, neuromodulation may be part of a vaccination protocol.

The vaccination protocol may including administering a vaccine that may be a vaccine for adenovirus, anthrax, AVA (BioThrax) cholera, Vaxchora, diphtheria, DTaP (Daptacel, Infanrix) hepatitis A, HepA (Havrix, Vaqta) hepatitis B, HepB (Engerix-B, Recombivax HB, Heplisav-B) *Haemo-*

*philus influenzae* type b (Hib) Hib (ActHIB, PedvaxHIB, Hiberix), human papillomavirus (HPV), seasonal influenza, measles, meningococcal, mumps, pertussis, pneumococcal, polio, rabies, rotavirus, rubella, Shingles, smallpox, tetanus, tuberculosis, typhoid fever, varicella, yellow fever, or SARS-CoV-2. The vaccination protocol may include administering a vaccine that may be a virus, or a virus-like particle vaccine, a protein vaccine, an mRNA vaccine and/or a DNA vaccine. The vaccine may include polypeptide chains or nucleic acid sequences coding polypeptide chains that are specific to SARS-CoV-2 or variants thereof.

Provided herein are techniques for neuromodulation based on direct and focused stimulation of immune-associated tissue, e.g., lymph node tissue, spleen tissue, etc. The present techniques may be used in conjunction with lymph node neuromodulation or modulation of any neuroimmune interfaces (e.g., the junction or synapse between an axon terminal and an immune cell). In addition, direct modulation of immune cells themselves is also contemplated, e.g., immune cells that are not part of a junction with a neuron. While certain embodiments of the disclosure are presented in the context of neuroimmune modulation, it should be understood that the disclosed techniques may be used in conjunction with other target tissues and with other types of non-neuronal cells. As provided herein, non-neuronal cells may include immune cells, muscular cells, secretory cells, etc. In addition, neuroimmune interfaces that may control antibody production or the functional state of lymphocytes may be modulated via ultrasound or other neuromodulating energy.

Figure 22:
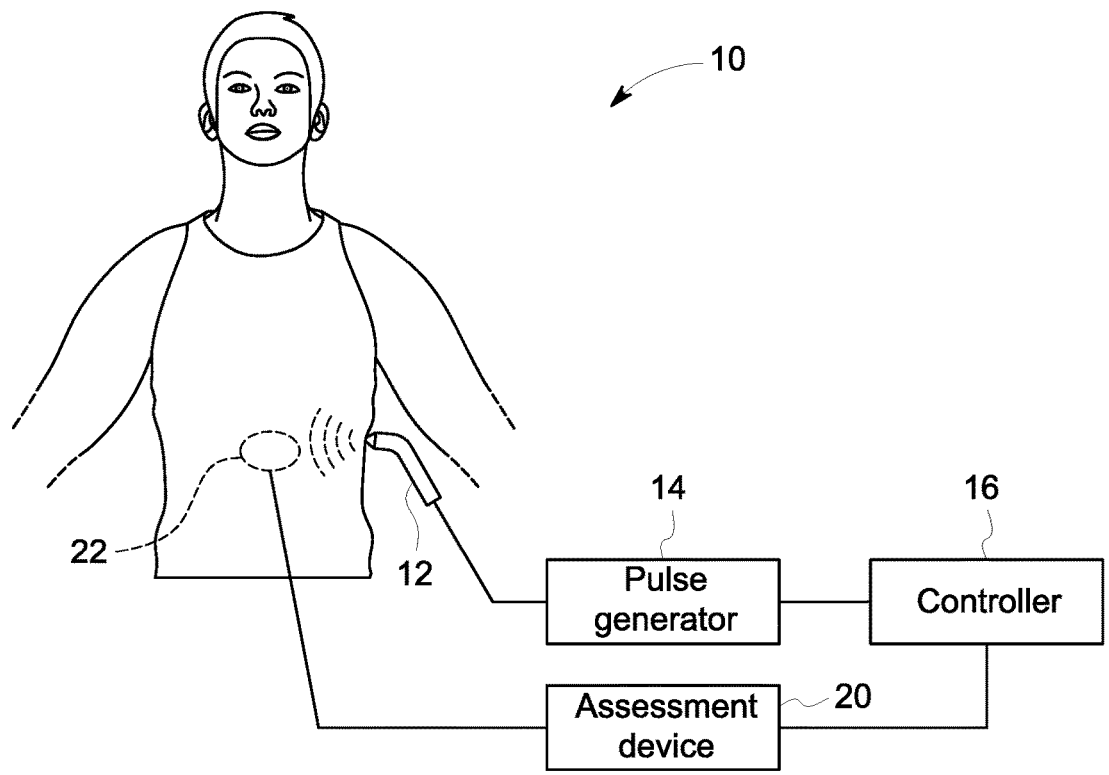
FIG. 22 is a schematic representation of a neuromodulation system used in conjunction with a vaccination protocol according to embodiments of the disclosure.

The disclosed neuromodulation techniques may be used in conjunction with a neuromodulation system. FIG. 22 is a schematic representation of a system 10 for neuromodulation to achieve neurotransmitter release and/or activate components (e.g., the presynaptic cell, the postsynaptic cell) of one or more synapses in a region of interest in response to an application of energy. For example, one of more end terminal axons of peripheral nerves of the lymph nodes or spleen may be modulated using focused ultrasound. The depicted system includes a pulse generator 14 coupled to an energy application device 12 (e.g., an ultrasound transducer). The energy application device 12 is configured to receive energy pulses, e.g., via leads or wireless connection, that in use are directed to a region of interest of an internal tissue or an organ of a subject, which in turn results in a targeted physiological outcome. In certain embodiments, the pulse generator 14 and/or the energy application device 12 may be implanted at a biocompatible site (e.g., the abdomen), and the lead or leads couple the energy application device 12 and the pulse generator 14 internally. For example, the energy application device 12 may be a MEMS transducer, such as a capacitive micromachined ultrasound transducer.

In certain embodiments, the energy application device 12 and/or the pulse generator 14 may communicate wirelessly, for example with a controller 16 that may in turn provide instructions to the pulse generator 14. In other embodiments, the pulse generator 14 may be an extracorporeal device, e.g., may operate to apply energy transdermally or in a noninvasive manner from a position outside of a subject's body, and may, in certain embodiments, be integrated within the controller 16. In embodiments in which the pulse generator 14 is extracorporeal, the energy application device 12 may be operated by a caregiver and positioned at a spot on or above a subject's skin such that the energy pulses are delivered transdermally to a desired internal tissue. Once positioned to apply energy pulses to the desired site, the system 10 may initiate neuromodulation to achieve targeted physiological outcome or clinical effects as generally disclosed herein.

In certain embodiments, the system 10 may include an assessment device 20 that is coupled to the controller 16 and assesses characteristics that are indicative of whether the targeted physiological outcome of the modulation have been achieved. In one embodiment, the targeted physiological outcome may be local. For example, the modulation may result in local tissue or function changes, such as tissue structure changes, local change of concentration of certain molecules, tissue displacement, increased fluid movement, etc. In an embodiment, the targeted physiological outcome may be a change in size of a lymph node as a result of targeting peripheral nerves in a lymph node and indicative of immune upregulation or immune boosting.

The modulation may result in systemic or non-local changes, and the targeted physiological outcome may be related to a change in concentration of circulating molecules or a change in a characteristic of a tissue that does not include the region of interest to which energy was directly applied. In one example, the displacement may be a proxy measurement for a desired modulation, and displacement measurements below an expected displacement value may result in modification of modulation parameters until an expected displacement value is induced. Accordingly, the assessment device 20 may be configured to assess concentration changes in some embodiments. In some embodiments, the assessment device 20 may be an imaging device configured to assess changes in organ size and/or position. While the depicted elements of the system 10 are shown separately, it should be understood that some or all of the elements may be combined with one another. Further, some or all of the elements may communicate in a wired or wireless manner with one another.

Based on the assessment, the modulation parameters of the controller 16 may be altered. For example, if a desired modulation is associated with a change in concentration (circulating concentration or tissue concentration of one or more molecules) within a defined time window (e.g., 5 minutes, 30 minutes after a procedure of energy application starts) or relative to a baseline at the start of a procedure, a change of the modulation parameters such as pulse frequency or other parameters may be desired, which in turn may be provided to the controller 16, either by an operator or via an automatic feedback loop, for defining or adjusting the energy application parameters or modulation parameters of the pulse generator 14.

The system 10 as provided herein may provide energy pulses according to various modulation parameters and as part of a treatment protocol. For example, the modulation parameters may include various stimulation time patterns, ranging from continuous to intermittent. With intermittent stimulation, energy is delivered for a period of time at a certain frequency during a signal-on time. The signal-on time is followed by a period of time with no energy delivery, referred to as signal-off time. The modulation parameters may also include frequency and duration of a stimulation application. The application frequency may be continuous or delivered at various time periods, for example, within a day or week. The treatment protocol duration may last for various time periods, including, but not limited to, from a few minutes to several hours. In certain embodiments, treatment duration with a specified stimulation pattern may last for one hour, repeated at, e.g., 72 hour intervals. In certain embodiments, treatment may be delivered at a higher frequency, say every three hours, for shorter durations, for example, 30 minutes. The application of energy, in accordance with modulation parameters, such as the treatment duration and frequency, may be adjustably controlled to achieve a desired result.

The focused ultrasound energy may be focused on a region of interest 22, which may be an internal structure, tissue, or an organ. For example, the region of interest may include one or more peripheral axon terminals and to in turn impact immune cell or marker levels and/or to impact immune regulation pathways. Neuromodulation of immune tissue and assessment of the effects of the neuromodulation may be as disclosed in U.S. Patent Publication No. 20190117977, which is incorporated by reference herein in its entirety for all purposes. In present techniques, one or more energy pulses are applied to the subject's internal tissue comprising axon terminals that include axoextracellular synapses or neuronal junctions with other cell types, interstitial fluid, or body fluid, e.g., at synapses between a neuronal cell and a non-neuronal cell, whereby applying energy to synapse causes direct activation of the presynaptic axon terminals and/or direct activation at the postsynaptic cell to cause a targeted physiological outcome. In one example, stimulation of axon terminals releases neurotransmitter/neuropeptide or induces altered neurotransmitter release in a vicinity of neighboring non-neuronal cells and modulates cell activity of the neighboring or nearby non-neuronal cells, including the postsynaptic cells. Further, via such modulation, modulation of other tissue structures or organs may be achieved, without direct stimulation. In one embodiment, direct energy application to a relatively small region of an organ (e.g., a volume less than 25% of the total organ volume) may be used to trigger action potentials in afferent neurons that project into different areas of the brain (e.g., the hypothalamus). However, this result may be achieved without direct brain stimulation of synapse-rich regions. The direct brain stimulation may result in undesired activation of other pathways that may interfere with or swamp a desired physiological outcome. Further, direct brain stimulation may involve invasive procedures. Accordingly, the present techniques permit granular activation of either brain activity or activity within an organ, tissue or structure in a manner that is more targeted and more specific than direct brain stimulation or electrical peripheral nerve stimulation. That is, granular activation permits activation of only certain molecules and not others and/or in certain tissues and not others in a predictable and targeted manner.

The energy application may be selected to preferentially trigger a release of one or more molecules such as neurotransmitters from the nerve within the synapse. In one embodiment, energy may be applied to two or more regions of interest 22. In some embodiments, the energy application parameters may be chosen to induce preferential activation of either neural or non-neuronal components within the tissue directly receiving energy to induce a desired combined physiological effect. In certain embodiments, the energy may be focused or concentrated within a volume of less than about 25 mm³. In certain embodiments, the energy may be focused or concentrated within a volume of about 0.5 mm³-50 mm³. A focal volume and a focal depth for focusing or concentrating the energy within the region of interest 22 may be influenced by the size/configuration of the energy application device 12. The focal volume of the energy application may be defined by the field of focus of the energy application device 12.

As provided herein, the energy may be substantially applied only to the region or regions of interest 22 to preferentially activate the synapse in a targeted manner to achieve targeted physiological outcomes and is not substantially applied in a general or a nonspecific manner across the entire tissue. Accordingly, only a subset of a plurality of axon terminals in an organ may be exposed to the direct energy application. For example, the regions of interest within organs containing either blood vessels, nerves, or other anatomical landmarks may be spatially selected and used to identify areas with specific axon terminals and synapses. In one embodiment, the region of interest is selected by identifying a splenic artery and spatially selecting an area close to or parallel to the splenic artery. The region of interest 22 may be selected based on factors including, but not limited to, historical or experimental data (e.g., data showing an association of a particular location with a desired or targeted physiological outcome). Alternatively or additionally, the system 10 may apply energy to different regions of interest until the desired targeted physiological effect is achieved. In one example, the region of interest may be in an organ or structure, such as a spleen, liver, pancreas, or gastrointestinal tissue. In another example, the regions of interest may be in a lymph system tissue. The region of interest may include a site of blood vessel or nerve entry into an organ, a tissue type within an organ, an interior or edge of an organ, or a suborgan structure, by way of non-limiting example. In certain embodiments, the anatomical feature may include a liver porta hepatis, suborgans of a gastrointestinal tract (stomach, small intestines, large intestines), a pancreatic duct, or a splenic white pulp.

Figure 23:
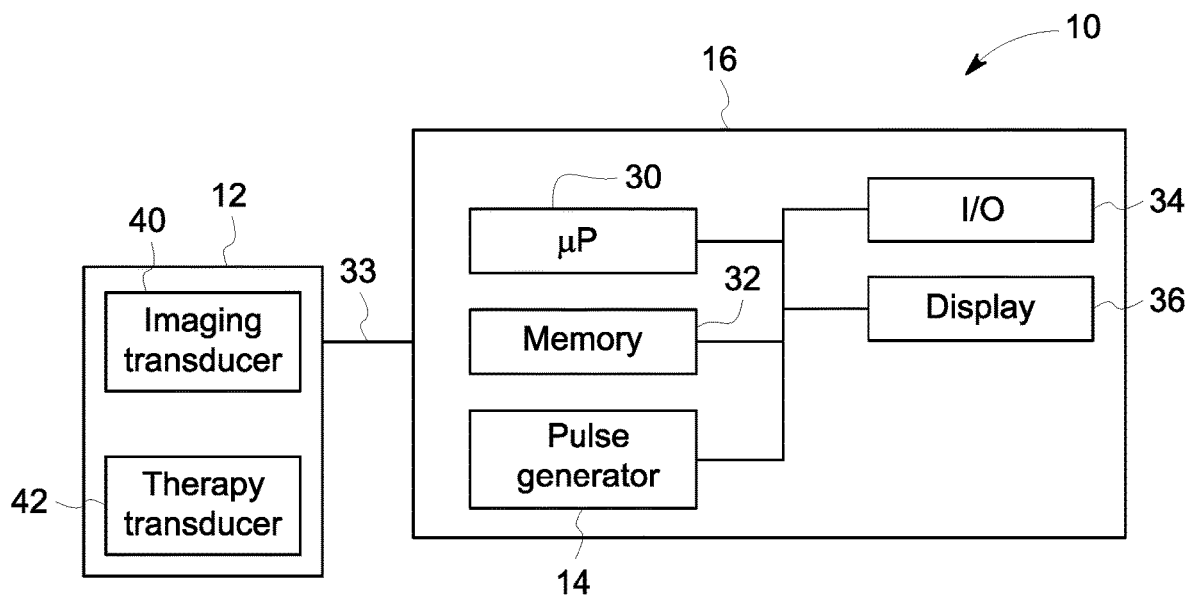
FIG. 23 is a block diagram of the neuromodulation system of FIG. 22 according to embodiments of the disclosure.

FIG. 23 is a block diagram of certain components of the system 10. As provided herein, the system 10 for neuromodulation may include a pulse generator 14 that is adapted to generate a plurality of energy pulses for application to a tissue of a subject. The pulse generator 14 may be separate or may be integrated into an external device, such as a controller 16. The controller 16 includes a processor 30 for controlling the device. Software code or instructions are stored in memory 32 of the controller 16 for execution by the processor 30 to control the various components of the device. The controller 16 and/or the pulse generator 14 may be connected to the energy application device 12 via one or more leads 33 or wirelessly The controller 16 also includes a user interface with input/output circuitry 34 and a display 36 that are adapted to allow a clinician to provide selection inputs or modulation parameters to modulation programs. Each modulation program may include one or more sets of modulation parameters including pulse amplitude, pulse width, pulse frequency, etc. The pulse generator 14 modifies its internal parameters in response to the control signals from controller device 16 to vary the stimulation characteristics of energy pulses transmitted through lead 33 to an subject to which the energy application device 12 is applied. Any suitable type of pulse generating circuitry may be employed, including but not limited to, constant current, constant voltage, multiple-independent current or voltage sources, etc. The energy applied is a function of the current amplitude and pulse width duration. The controller 16 permits adjustably controlling the energy by changing the modulation parameters and/or initiating energy application at certain times or cancelling/suppressing energy application at certain times.

In one embodiment, the adjustable control of the energy application device is based on information about a concentration of one or more molecules in the subject (e.g., a circulating molecule, such as a biomarker associated with immune function or a population of immune cells). If the information is from the assessment device 20, a feedback loop may drive the adjustable control. For example, if a lymph marker LYVE-1, Prox-1, podoplanin, and VEGFR3, as measured by the assessment device 20, is above a predetermined threshold or range, the controller 16 may initiate energy application to a region of interest and with modulation parameters that are associated with a change in the biomarker. The initiation of energy application may be triggered by the biomarker drifting above or below a predetermined (e.g., desired) threshold or outside a predefined range. In another embodiment, the adjustable control may be in the form of altering modulation parameters when an initial application of energy does not result in an expected change in a targeted physiological outcome (e.g., concentration of a molecule of interest) within a predetermined time frame (e.g., 1 hour, 2 hours, 4 hours, 1 day).

In one embodiment, the memory 32 stores different operating modes that are selectable by the operator. For example, the stored operating modes may include instructions for executing a set of modulation parameters associated with a particular treatment site. Different sites may have different associated modulation parameters. Rather than having the operator manually input the modes, the controller 16 may be configured to execute the appropriate instruction based on the selection. In another embodiment, the memory 32 stores operating modes for different types of treatment. For example, activation may be associated with a different stimulating pressure or frequency range relative to those associated with depressing or blocking tissue function. In a specific example, when the energy application device is an ultrasound transducer, the time-averaged power (temporal average intensity) and peak positive pressure are in the range of 1 $mW/cm^2$-30,000 $mW/cm^2$ (temporal average intensity) and 0.1 MPa to 7 MPa (peak pressure). In one example, the temporal average intensity is less than 35 $W/cm^2$ in the region of interest to avoid levels associated with thermal damage & ablation/cavitation. In another specific example, when the energy application device is a mechanical actuator, the amplitude of vibration is in the range of 0.1 to 10 mm. The selected frequencies may depend on the mode of energy application, e.g., ultrasound or mechanical actuator.

In another embodiment, the memory 32 stores a calibration or setting mode that permits adjustment or modification of the modulation parameters to achieve a desired result. In one example, the stimulation starts at a lower energy parameter and increases incrementally, either automatically or upon receipt of an operator input. In this manner, the operator may achieve tuning of the induced effects as the modulation parameters are being changed.

The system may also include an imaging device, such as imaging transducer 40 that facilitates focusing the energy application device 12 by acquiring imaging data when the energy application device 12 is operating in an imaging mode under instructions from the controller 16. The energy application device 12 may include an ultrasound therapy transducer 42 that is capable of applying focused ultrasound energy to a target that is within the region of interest 22 when operating in a therapy mode under instructions from the controller 16. The energy application device 12 may include control circuitry for controlling the imaging transducer 40 and/or the ultrasound therapy transducer 42. The control circuitry of the processor 30 may be integral to the energy application device 12 (e.g., via an integrated controller 16) or may be a separate component. The imaging transducer 40 may also be configured to acquire image data to assist with spatially selecting a desired or targeted region of interest and focusing the applied energy on the region of interest of the target tissue or structure.

In one embodiment, the imaging device (transducer 40) may be integrated with or the same device as the energy application device 12 such that different ultrasound parameters (frequency, aperture, or energy) are applied for selecting (e.g., spatially selecting) a region of interest and for focusing energy to the selected region of interest for targeting and subsequently neuromodulation. In another embodiment, the memory 32 stores one or more targeting or focusing modes that is used to spatially select the region of interest within an organ or tissue structure. Spatial selection may include selecting a subregion of an organ to identify a volume of the organ that corresponds to a region of interest. Spatial selection may rely on image data as provided herein. In one embodiment, the controller 16 may be programmed to automatically identify or select the region of interest based on the image data. In an embodiment, the image data may be displayed on the display 36, and an operator may designate portions of the image that correspond to the region of interest. Based in the user input, the controller 16 may select the region of interest. Based on the spatial selection, the energy application device 12 may be focused on the selected volume corresponding to the region of interest. For example, the energy application device 12 may be configured to first operate in the imaging mode to apply imaging mode energy that is used to capture image data to be used for identifying the region of interest. The imaging mode energy is not at levels and/or applied with modulation parameters suitable for preferential activation. However, once the region of interest is identified, the controller 16 may then operate in a treatment mode according to the modulation parameters associated with neuromodulation as provided herein.

The controller 16 may also be configured to receive inputs related to the targeted physiological outcomes as an input to the selection of the modulation parameters. For example, when an imaging modality is used to assess a tissue characteristic, the controller 16 may be configured to receive a calculated index or parameter of the characteristic. Based on whether the index or parameter is above or below a predefined threshold, the modulation parameters may be modified. In one embodiment, the parameter can be a measure of tissue displacement of the affected tissue or a measure of depth of the affected tissue. Other parameters may include assessing a concentration of one or more molecules of interest (e.g., assessing one or more of a change in concentration relative to a threshold or a baseline/control, a rate of change, determining whether concentration is within a desired range). Further, the energy application device 12 may operate under control of the controller 16 to a) acquire image data of a tissue that may be used to spatially select a region of interest within the target tissue b) apply the modulating energy to the region of interest and c) acquire image data to determine that the targeted physiological outcome has occurred (e.g., via displacement measurement). In such an embodiment, the imaging device, the assessment device 20 and the energy application device 12 may be the same device.

In another implementation, a desired modulation parameter set may also be stored by the controller 16. In this manner, subject-specific parameters may be determined. Further, the effectiveness of such parameters may be assessed over time. If a particular set of parameters is less effective over time, the subject may be developing insensitivity to activated pathways. If the system 10 includes an assessment device 20, the assessment device 20 may provide feedback to the controller 16. In certain embodiments, the feedback may be received from a user or an assessment device 20 indicative of a characteristic of the target physiological outcome. The controller 16 may be configured to cause the energy application device to apply the energy according to modulation parameters and to dynamically adjust the modulation parameters based on the feedback. For example, based on the feedback, the processor 16 may automatically alter the modulation parameters (e.g., the frequency, amplitude, or pulse width of an ultrasound beam or mechanical vibration) in real time and responsive to feedback from the assessment device 20.

The disclosed techniques may be used in assessment of neuromodulation effects, which in turn may be used as an input or a feedback for selecting or modifying neuromodulation parameters. The disclosed techniques may use direct assessments of tissue condition or function as the targeted physiological outcomes. The assessment may occur before (i.e., baseline assessment), during, and/or after the neuromodulation.

The assessment techniques may include at least one of functional magnetic resonance imaging, diffusion tensor magnetic resonance imaging, positive emission tomography, or acoustic monitoring, thermal monitoring. The assessment techniques may also include protein and/or marker concentration assessment. The images from the assessment techniques may be received by the system for automatic or manual assessment. Based on the image data, the modulation parameters may also be modified. For example, a change in organ size or displacement may be utilized as a marker of local neurotransmitter concentration, and used as a surrogate marker for exposure of local cells to phenotype modulating neurotransmitters, and effectively as a marker of predicted effect on immune pathways. The local concentration may refer to a concentration within a field of focus of the energy application.

Additionally or alternatively, the system may assess the presence or concentration of one or more molecules or cells in the tissue or circulating in the blood. The concentration in the tissue may be referred to as a local concentration or resident concentration. Tissue may be acquired by a fine needle aspirate, and the assessment of the presence or levels of molecules of interest may be performed by any suitable technique known to one of ordinary skilled in the art. As provided herein, the assessment may be based on a total white blood cell counts (WBC) along with specific cell counts for neutrophils (NE), lymphocytes (LV), monocytes (MO), and basophils (BA) representing subsets of the white blood cell populations. Immune markers of interest may include cytokines (TNF-alpha, IL-1 beta, IL-10).

In other embodiments, the targeted physiological outcomes may include, but are not limited to, tissue displacement, tissue size changes, a change in concentration of one or more molecules (either local, non-local, or circulating concentration), a change in gene or marker expression, afferent activity, and cell migration, etc. For example, tissue displacement (e.g., a blood vessel displacement of an adjacent artery) may occur as a result of energy application to the tissue. By assessing the tissue displacement to the spleen or lymph node (e.g., via imaging), other effects may be estimated. For example, a certain displacement may be characteristic of a particular change in molecule concentration.

Figure 24:
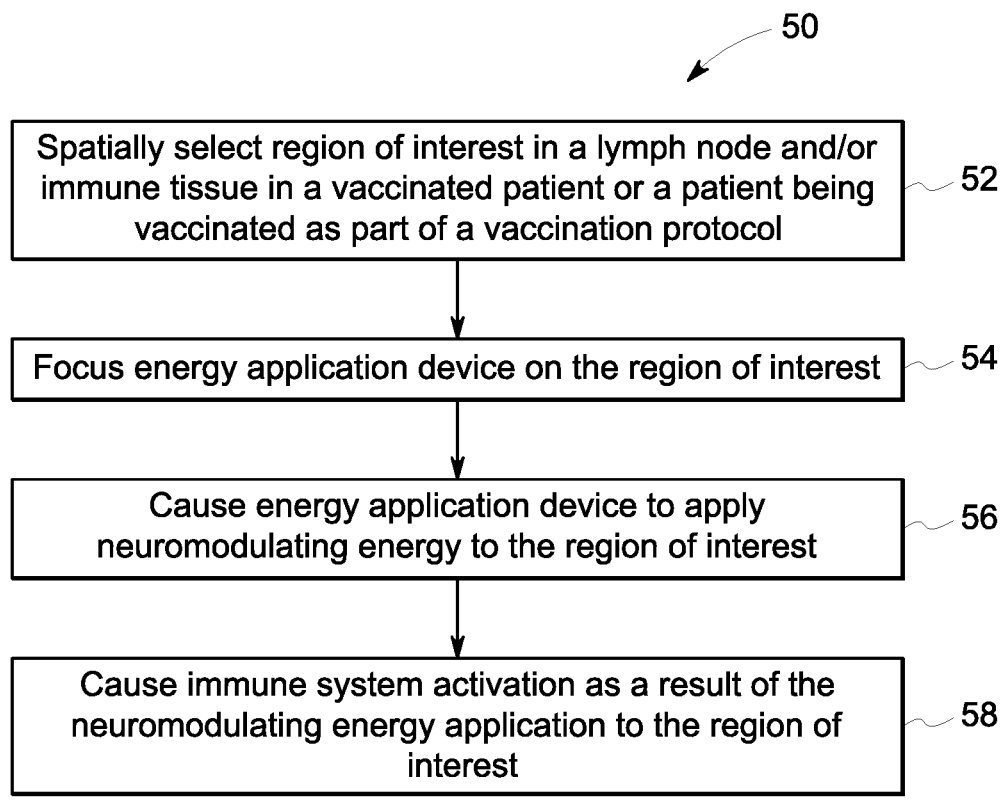
FIG. 24 is a flow diagram of a method of neuromodulation used in conjunction with a vaccination protocol according to embodiments of the disclosure.

FIG. 24 is a flow diagram of a method 50 for neuromodulation of used as an immune booster for a vaccination protocol. In the method 50, image data of a vaccinated subject or a subject being concurrently vaccinated is acquired at step 52 to identify the region of the lymph node in the subject likely to include the desired peripheral nerve axon terminal portion. The region of interest may include only a portion of a peripheral nerve that includes the junction of the nerve with a non-neuronal cell in the lymph node or spleen.

The energy application device is positioned such that the energy pulses are focused at the desired region of interest at step 54, and the pulse generator applies a plurality of energy pulses to the region of interest of the target tissue at step 56 to preferentially activate at least a portion of a peripheral nerve that is positioned in the region of interest, e.g., to stimulate the nerve axon or axons in the region of interest to release neurotransmitters and/or induce altered neurotransmitter release and/or induce altered activity as provided herein. At step 58, the application of neuromodulating energy causes immune system activation to promote the protective vaccine effects, e.g., relative to a control in which no neuromodulating energy is applied.

In embodiments, the neuromodulation of the method 50 is applied concurrently with or substantially concurrently with vaccination. Thus, the vaccine protocol includes administering a vaccine (e.g., injection, nasal administration, oral administration) and, within hours of the vaccine administration-before or after-applying neuromodulating energy, e.g., via a focused ultrasound device. In embodiments, the neuromodulating energy is applied a same day as the vaccine is administered. In embodiments, the neuromodulating energy is applied before the vaccine is administered to prime an immune response. In embodiments, the neuromodulating energy is applied after the vaccine is administered, e.g., a day after, two days after, a week after, two weeks after. In embodiments, the neuromodulating energy is applied once, twice, or more as part of the vaccination protocol. In one example, the neuromodulating energy is applied 24 hours before treatment, 1 hour before treatment, 1 hour after treatment, and/or 24 hours after treatment.

In an embodiment, the region of interest is in a lymph node or spleen. In an embodiment, the region of interest is in a gastrointestinal tissue. In certain embodiments, the method may include a step of assessing the effect of the stimulation. For example, one or more direct or indirect assessments of a state of tissue function or condition may be used. The assessment may be a concentration of an immune molecule relative to baseline. Based on the tissue function as assessed, the modulation parameters of the one or more energy pulses may be modified (e.g., dynamically or adjustably controlled) to achieve the targeted physiological outcome. In one example, the proxy marker is a circulating antibody concentration, such as a circulating IgG antibody concentration. Increased antibody production is associated with successful adjuvant effects of the neuromodulation.

In one embodiment, assessments may be performed before and after applying energy pulses to assess the immune activation effects using proxy markers of immune function. For example, if the marker is within or associated with a desired physiological outcome, the energy applied during neuromodulation may be stepped back to a minimum level that supports the desired outcome. If the change in the characteristic relative to the threshold is associated with insufficient change in marker, certain modulation parameters, including, but not limited to, the modulation amplitude or frequency, the pulse shape, the stimulation pattern, and/or the stimulation location may be changed.

Further, the assessed characteristic or condition may be a value or an index, for example, a flow rate, a concentration, a cell population (e.g., a change in white blood cell locations or characteristics), or any combination thereof, which in turn may be analyzed by a suitable technique. For example, a relative change exceeding a threshold may be used to determine if the modulation parameters are modified. The desired modulation may be assessed via a measured clinical outcome, such as a presence or absence of an increase in tissue structure size (e.g., colon tissue characteristics) or a change in concentration of one or more released molecules (e.g., relative to the baseline concentration before the neuromodulation). In one embodiment, a desired modulation may involve an increase in concentration above a threshold, e.g., above a about 50%, 100%, 200%, 400%, 1000% increase in concentration relative to baseline. For blocking treatments, the assessment may involve tracking a decrease in concentration of a molecule over time, e.g., at least a 10%, 20%, 30%, 50%, or 75% decrease in the molecule of interest. Further, for certain subjects, the desired blocking treatment may involve keeping a relatively steady concentration of a particular molecule in the context of other clinical events that may tend to increase the concentration of the molecule. That is, desired blocking may block a potential increase. The increase or decrease or other induced and measurable effect may be measured within a certain time window from the start of a treatment, e.g., within about 5 minutes, within about 30 minutes. In certain embodiments, if the neuromodulation is determined to be desired, the change in the neuromodulation is an instruction to stop applying energy pulses. In another embodiment, one or more parameters of the neuromodulation are changed if the neuromodulation is not desired. For example, the change in modulation parameters may be an increase in pulse repetition frequency, such as a stepwise increase in frequency of 10-100 Hz and assessment of the desired characteristic until a desired neuromodulation is achieved. In another implementation, a pulse width may be changed. In other embodiments, two or more of the parameters may be changed together, in parallel or in series. If the neuromodulation is not desired after multiple parameter changes, the focus (i.e., the site) of energy application may be changed.

Technical effects of the disclosed embodiments include techniques for targeting regulation pathways that are disrupted by SARS-CoV-2 infection using focused ultrasound to improve patient outcomes. The disclosed embodiments also include vaccination protocols with neuromodulation to provide adjuvant effects. The disclosed embodiments also include treatment protocols that disrupt or block immune responses in infected individuals, e.g., to disrupt a cytokine storm.

This written description uses examples, including the best mode, and also to enable any person skilled in the art to practice the disclosed embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for modulating an immune response in a subject, comprising:
    applying ultrasound energy to an internal tissue of the subject, wherein the internal tissue is a gastrointestinal tissue;
    measuring a change in concentration of circulating CCK in the subject after applying the ultrasound energy; and
    determining, based on the change, that the applied ultrasound energy caused the change in concentration to the circulating CCK.

2. The method of claim 1, wherein the internal tissue further comprises a liver tissue.

3. The method of claim 1, wherein the applied ultrasound energy is focused or concentrated within a volume of less than about 25 mm$^3$ of the internal tissue.

4. The method of claim 1, wherein applying the ultrasound energy causes a decrease in a concentration of circulating IL-6 relative to a baseline concentration before the energy is applied.

5. The method of claim 1, wherein cleavage of the c-terminal dipeptide of CCK by angiotensin-converting enzyme (ACE) is associated with class switching of antibodies.

* * * * *